(12) United States Patent
Kato et al.

(10) Patent No.: US 11,052,011 B2
(45) Date of Patent: Jul. 6, 2021

(54) STANDING-UP ASSISTANCE APPARATUS, STANDING-UP ASSISTANCE METHOD, AND NON-TRANSITORY COMPUTER-READABLE RECORDING MEDIUM

(71) Applicant: Panasonic Intellectual Property Management Co., Ltd., Osaka (JP)

(72) Inventors: Yusuke Kato, Chiba (JP); Tsuyoshi Inoue, Nara (JP); Hiroyuki Motoyama, Shiga (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 792 days.

(21) Appl. No.: 15/685,151

(22) Filed: Aug. 24, 2017

(65) Prior Publication Data

US 2018/0064599 A1    Mar. 8, 2018

(30) Foreign Application Priority Data

Sep. 2, 2016   (JP) .............................. JP2016-172297
Mar. 13, 2017  (JP) .............................. JP2017-047313

(51) Int. Cl.
  *A61H 1/02*   (2006.01)
  *B25J 9/00*   (2006.01)
  (Continued)

(52) U.S. Cl.
  CPC .............. *A61H 1/0237* (2013.01); *A61B 5/68* (2013.01); *A61G 5/14* (2013.01); *A61H 1/024* (2013.01);
  (Continued)

(58) Field of Classification Search
  CPC . A61B 5/04012; A61B 5/1116; A61B 5/6812; A61B 5/0488; A61B 5/68;
  (Continued)

(56) References Cited

U.S. PATENT DOCUMENTS

2006/0211956 A1   9/2006   Sankai
2008/0161937 A1   7/2008   Sankai
(Continued)

FOREIGN PATENT DOCUMENTS

CN         1838933       9/2006
CN         101111211     1/2008
(Continued)

OTHER PUBLICATIONS

English Translation of Chinese Search Report dated Apr. 14, 2021 in related Chinese Patent Application No. 201710604982.9.

*Primary Examiner* — Suba Ganesan
*Assistant Examiner* — Aren Patel
(74) *Attorney, Agent, or Firm* — Wenderoth, Lind & Ponack, L.L.P.

(57) ABSTRACT

A standing-up assistance apparatus includes a first sensor that measures a muscle potential of a lower leg of a user, a second sensor that measures a knee angle of the user, a processor that determines whether starting to assist the user in a standing-up motion from a seated state is possible, based on, at least, the measured muscle potential and the measured knee angle, and outputs an instruction signal if the processor determines that starting to assist the user in the standing-up motion is possible, and an assistance mechanism. The assistance mechanism starts assisting the user in the standing-up motion when the assistance mechanism receives the instruction signal from the processor.

24 Claims, 27 Drawing Sheets

(51) Int. Cl.
*B25J 13/08* (2006.01)
*B25J 9/16* (2006.01)
*A61G 5/14* (2006.01)
*A61B 5/00* (2006.01)
*A61B 5/107* (2006.01)
*A61B 5/11* (2006.01)
*A61B 5/389* (2021.01)

(52) U.S. Cl.
CPC ........... *B25J 9/0006* (2013.01); *B25J 9/1694* (2013.01); *B25J 13/088* (2013.01); *A61B 5/1071* (2013.01); *A61B 5/1116* (2013.01); *A61B 5/389* (2021.01); *A61B 5/4585* (2013.01); *A61B 2562/0219* (2013.01); *A61H 2201/164* (2013.01); *A61H 2201/165* (2013.01); *A61H 2201/1642* (2013.01); *A61H 2201/1659* (2013.01); *A61H 2201/5007* (2013.01); *A61H 2201/5058* (2013.01); *A61H 2201/5069* (2013.01); *A61H 2201/5079* (2013.01); *A61H 2201/5084* (2013.01); *A61H 2203/0406* (2013.01); *A61H 2205/106* (2013.01); *A61H 2205/108* (2013.01); *A61H 2230/605* (2013.01); *G05B 2219/40305* (2013.01)

(58) Field of Classification Search
CPC ........ A61H 1/02; A61H 1/0237; A61H 1/024; A61H 3/00; A61H 3/02; A61H 2201/1642; A61H 2201/165; A61H 2201/5007; A61H 2201/5035; A61H 2201/5041; A61H 2201/5064; A61H 2201/5079; A61H 2201/5084; A61H 2205/106; B25J 9/0006; B25J 9/1694; B25J 13/088; A61G 5/14
USPC .......................................................... 601/35
See application file for complete search history.

(56) References Cited

U.S. PATENT DOCUMENTS

2010/0271051 A1* 10/2010 Sankai .................. A61H 3/008
                                                                    324/679
2016/0235616 A1    8/2016 Goffer et al.

FOREIGN PATENT DOCUMENTS

| CN | 103328051 | 9/2013 |
| JP | 2005-230099 | 9/2005 |
| JP | 2010-253048 | 11/2010 |

\* cited by examiner

| TIME (s) | USER ID | MUSCLE POTENTIAL VALUE OF ANTERIOR TIBIAL MUSCLE (V) | MUSCLE POTENTIAL VALUE OF MEDIAL GREAT MUSCLE (V) | TRUNK FORWARD TILTING ANGLE (deg.) |
|---|---|---|---|---|
| 13:45:30.00 | 1 | 0.000639 | −0.000003 | 18.32 |
| 13:45:30.01 | 1 | 0.000416 | 0.000002 | 18.49 |
| 13:45:30.02 | 1 | 0.000208 | 0.000007 | 18.74 |
| 13:45:30.03 | 1 | 0.000104 | 0.000014 | 19.00 |
| ⋮ | ⋮ | ⋮ | ⋮ | ⋮ |

FIG. 9A

| ORDER OF ACQUISITION | MUSCLE POTENTIAL VALUE OF ANTERIOR TIBIAL MUSCLE (V) | TIME (s) |
|---|---|---|
| 1 | 0.000639 | 0 |
| 2 | 0.000416 | 0.001 |
| 3 | 0.000208 | 0.002 |
| 4 | 0.000104 | 0.003 |
| ⋮ | ⋮ | ⋮ |

FIG. 9B

| ORDER OF ACQUISITION | TRUNK FORWARD TILTING ANGLE (deg.) | TIME (s) |
|---|---|---|
| 1 | 19.378 | 0 |
| 2 | 19.620 | 0.01 |
| 3 | 19.869 | 0.02 |
| 4 | 20.122 | 0.03 |
| ⋮ | ⋮ | ⋮ |

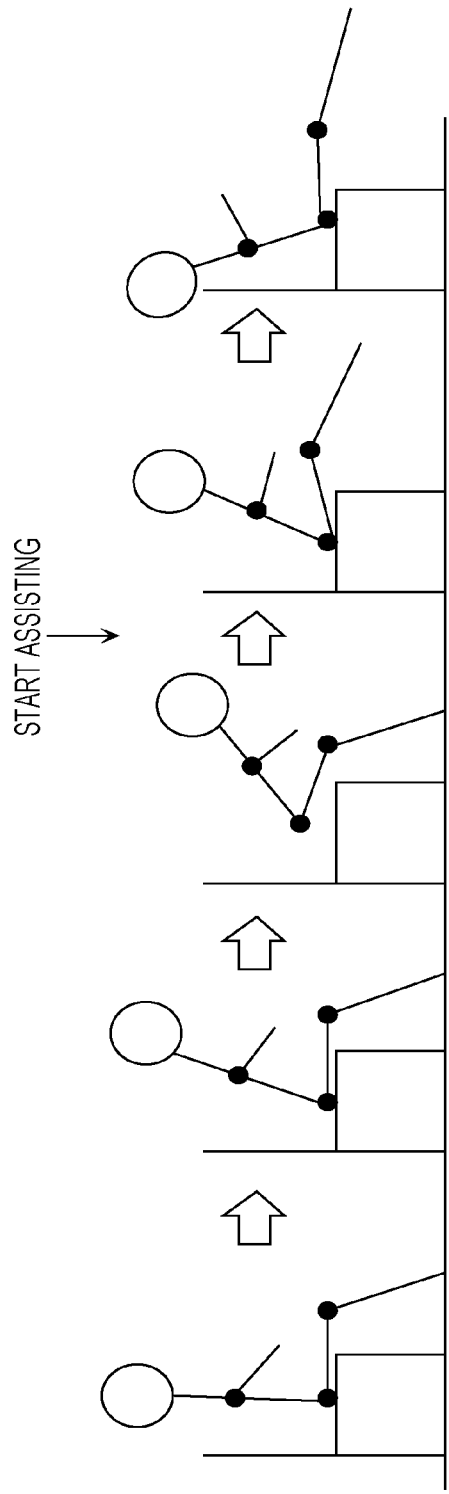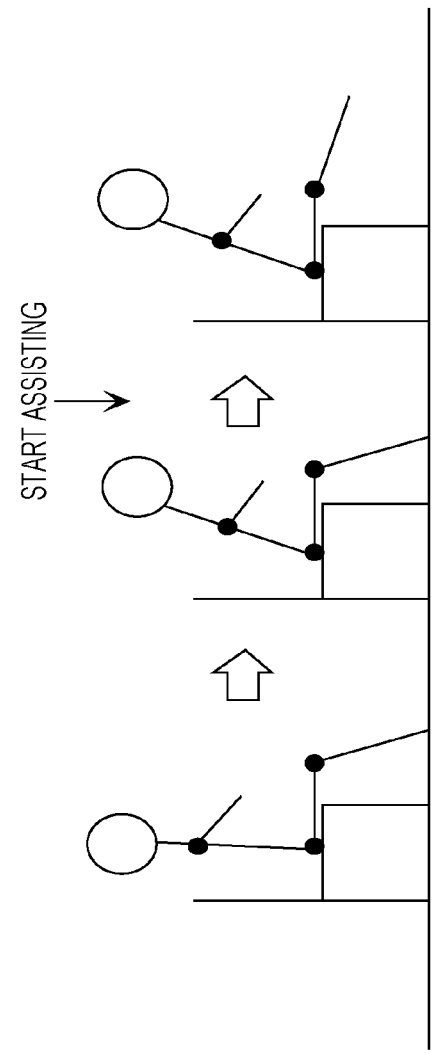

STANDING-UP ASSISTANCE APPARATUS, STANDING-UP ASSISTANCE METHOD, AND NON-TRANSITORY COMPUTER-READABLE RECORDING MEDIUM

BACKGROUND

1. Technical Field

The present disclosure relates to a standing-up assistance apparatus, a standing-up assistance method, and a non-transitory computer-readable recording medium for assisting a user in a standing-up motion.

2. Description of the Related Art

Japanese Unexamined Patent Application Publication No. 2010-253048 discloses a standing-up assistance apparatus (lower limb orthosis) that is worn around a lower limb of a user and assists a user in a standing-up motion by driving an actuator secured to the user's knee or waist.

The standing-up assistance apparatus disclosed in Japanese Unexamined Patent Application Publication No. 2010-253048 has difficulty in appropriately assisting a user in a standing-up motion.

SUMMARY

One non-limiting and exemplary embodiment provides a standing-up assistance apparatus that appropriately assists a user in a standing-up motion.

In one general aspect, the techniques disclosed here feature a standing-up assistance apparatus. The standing-up assistance apparatus includes a first sensor that measures a muscle potential of a lower leg of a user, a second sensor that measures a knee angle of the user, a processor that determines whether starting to assist the user in a standing-up motion from a seated state is possible, based on, at least, the measured muscle potential and the measured knee angle, and outputs an instruction signal if the processor determines that starting to assist the user in the standing-up motion is possible, and an assistance mechanism. The assistance mechanism starts to assist the user in the standing-up motion when the assistance mechanism receives the instruction signal from the processor.

In accordance with the disclosure, the user is appropriately assisted in the standing-up motion.

It should be noted that general or specific embodiments may be implemented as a system, a method, an integrated circuit, a computer program, a non-transitory computer readable recording medium, or any selective combination thereof. The non-transitory computer readable recording medium may include a non-volatile recording medium, such as a compact disk read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 9A illustrates another example of the information stored on the memory of the first embodiment;

FIG. 9B illustrates another example of the information stored on the memory of the first embodiment;

FIG. 15A illustrates an operation example in which the user breaks the balance of the body when assistance starts in a standing-up motion;

FIG. 15B illustrates a failure example of the standing-up motion;

DETAILED DESCRIPTION

Figure 1A:
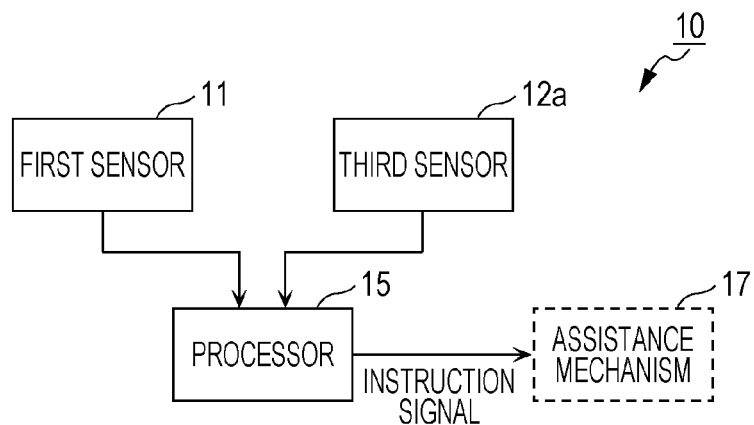
FIG. 1A is a functional block diagram diagrammatically illustrating a standing-up assistance apparatus of a first embodiment.

Underlying Knowledge Forming Basis of the Present Disclosure

The inventor has found that the standing-up assistance apparatus disclosed in Japanese Unexamined Patent Application Publication No. 2010-253048 described in "Description of the Related Art" section has difficulty as described below.

When a user is assisted in a standing-up motion with the standing-up assistance apparatus disclosed in Japanese Unexamined Patent Application Publication No. 2010-253048, care is to be exercised so that the user may not fall as a result of breaking the balance of the user's body. One of the causes that may break the body balance is that the user's posture that the user is supposed to take by the standing-up assistance apparatus prior to the standing-up motion is not correct. For this reason, before starting assistance, the standing-up assistance apparatus may have to recognize the user's posture and determine whether the user is able stand up in a manner free from falling. The standing-up assistance apparatus disclosed in Japanese Unexamined Patent Application Publication No. 2010-253048 measures the relative horizontal position of each foot with respect to the hips. If the relative horizontal position of each foot is within a predetermined range and each foot is planted on the floor, the standing-up assistance apparatus starts assisting the user in the standing-up motion.

The standing-up assistance apparatus disclosed in Japanese Unexamined Patent Application Publication No. 2010-253048 uses a planting sensor to determine whether the user's feet are planted on the floor. However, even if the user's feet are planted, the user may need to tighten the legs' muscles to impart tension to the lower legs in order to assist in the standing-up motion. The lower legs may not be sufficiently tensioned even with the user's feet planted. In such a case, the standing-up assistance apparatus is unable to cause the user to stand up even if the standing-up assistance apparatus starts assistance and causes the user to extend the knees. The standing-up assistance apparatus simply moves the lower leg forward. Even with a strong tension in the lower legs, the standing-up assistance apparatus has difficulty in causing the user to stand up if the user's knees are not appropriately bent.

To address the problem, the present disclosure provides a standing-up assistance apparatus. The standing-up assistance apparatus includes a first sensor that measures a muscle potential of a lower leg of a user, a second sensor that measures a knee angle of the user, a processor that determines whether starting to assist the user in a standing-up motion from a seated state is possible, based on, at least, the measured muscle potential and the measured knee angle, and outputs an instruction signal if the processor determines that starting to assist the user in the standing-up motion is possible, and an assistance mechanism. The assistance mechanism starts to assist the user in the standing-up motion when the assistance mechanism receives the instruction signal from the processor, More specifically, the assistance mechanism may determine that starting to assist the user in the standing-up motion is possible if a first condition that the measured muscle potential is equal to or higher than a first threshold value and a second condition that the measured knee angle is equal to or smaller than a second threshold value are concurrently satisfied.

Since the processor determines whether starting to assist the user in the standing-up motion is possible, based on the muscle potential and the knee angle of a lower leg of the user, the standing-up assistance apparatus may start assisting in the standing-up motion when the user's lower legs have a strong tension and the user's knees are appropriately bent. The standing-up assistance apparatus thus appropriately assists the user in the standing-up motion and allows the user to reliably stand up without failure in the standing-up motion.

The first sensor may measure a muscle potential of an anterior tibial muscle of the user as the muscle potential of the lower leg of the user.

The standing-up assistance apparatus is thus able to start assisting in the standing-up motion at the timing when the user's lower legs have a strong tension. The standing-up assistance apparatus thus causes the user to stand up in a stable way.

The second threshold value may be 60° or higher and 100° or lower.

The standing-up assistance apparatus may start assisting in the standing-up motion when the user appropriately bends the knees, in other words, the user is in a state that allows the user to stand up without any difficulty. As a result, a failure in the standing-up motion is controlled more.

The knee angle of the user measured by the second sensor may be the knee angle of the use's left knee or the knee angle of the user's right knee, whichever is smaller.

A determination as to whether starting to assist the user in the standing-up motion is possible is performed based on the knee angle of the left leg or the right leg of the user, whichever leg tensions the muscles. The user is thus allowed to stand up in a stable way.

In accordance with another aspect, there is provided a standing-up assistance apparatus. The standing-up assistance apparatus includes a first sensor that measures a muscle potential of a lower leg of a user, a second sensor that measures a knee angle of the user, a third sensor that measures a trunk forward tilting angle of the user, a processor that determines whether starting to assist the user in a standing-up motion from a seated state is possible, based on the measured muscle potential, the measured knee angle, and the measured trunk forward tilting angle, and outputs an instruction signal if the processor determines that starting to assist the user in the standing-up motion is possible, and an assistance mechanism that starts assisting the user in the standing-up motion when the instruction signal is output from the processor. The trunk forward tilting angle is an angle made between a vertical direction and the user's trunk and increases as the user's trunk tilts forward more.

The user's standing-up motion involves a forward tilting motion of the upper half of the user's body (namely, the user's trunk). If the upper half of the user's body is not sufficiently forward tilted, the user may suffer the risk of falling backward when the standing-up assistance apparatus starts assisting in the standing-up motion. The standing-up assistance apparatus disclosed in Japanese Unexamined Patent Application Publication No. 2010-253048 starts assisting in the standing-up motion without accounting for the posture of the upper half of the user's body. There is a possibility that the user falls as described above.

In the standing-up assistance apparatus of another aspect of the disclosure, the processor determines whether starting to assist the user in a standing-up motion from a seated state is possible, in accordance with the muscle potential of the user's lower leg, the knee angle, and the trunk forward tilting angle. As a result, the standing-up assistance apparatus may start assisting in the standing-up motion when the user tilts the trunk forward. The standing-up assistance apparatus appropriately assists the user in the standing-up motion and allows the user to stand up in a stable way with the occurrence of a fall of the user controlled.

The processor may determine that starting to assist the user in the standing-up motion is possible if a first condition that the measured muscle potential is equal to or higher than a first threshold value, a second condition that the measured knee angle is equal to or smaller than a second threshold value, and a third condition that the measured trunk forward tilting angle is equal to or larger than a third threshold value are concurrently satisfied.

The standing-up assistance apparatus does not start assisting the user in the standing-up motion if the knee angle is larger and the trunk forward tilting angle is smaller, but starts assisting if the knee angle is smaller and the trunk forward tilting angle is larger. This arrangement controls the risk that the user breaks the body balance and falls when the assistance in the standing-up motion starts with the user extending the user's legs forward and with the knee angle increased. This arrangement also controls the risk that the user falls backward when the assistance in the standing-up motion starts with the user not tilting the trunk forward.

The processor may set the first threshold value to be lower as the measured knee angle becomes smaller, and determine that starting to assist the user in the standing-up motion is possible if a first condition that the measured muscle potential is equal to or higher than a first threshold value, and a third condition that the measured trunk forward tilting angle is equal to or larger than a third threshold value are concurrently satisfied.

When the knee angle is larger, assisting the user in the standing-up motion is not started without a strong tension in the lower legs of the user. When the knee angle is smaller, assisting the user in the standing-up motion is started even with a weak tension in the lower legs of the user. This arrangement controls the risk that the user breaks the body balance and falls when the assistance in the standing-up motion starts under the condition that the tension of the lower leg of the user is not sufficiently strong with the user's legs extended forward and with the knee angle increased.

The processor may output a notification signal to prompt the user to bend the knees if each of the measured muscle potential and the measured trunk forward tilting angle changes periodically.

When each of the measured muscle potential and the measured trunk forward tilting angle changes periodically, the user may attempt to stand up. Since the knee angle is larger, the user is unable to stand up, and repeats attempting to stand up. In this state, the notification signal to prompt the user to bend the knees is output. In response to the notification signal, a voice message or text message to prompt the user to bend the knees is presented to the user. Then, the user bends the knees. When the knees are bent, in other words, when the knee angle becomes smaller, the first threshold value is set to be smaller, and the first condition tends to be more easily satisfied. As a result, the processor determines that starting to assist in the standing-up motion is possible, and the assistance mechanism assists the user in the standing-up motion. The user may thus easily stand up.

The standing-up assistance apparatus may include a fourth sensor that measures a trunk to thigh angle that is made between the user's trunk and thigh. The processor may modify the first threshold value in response to a change in each of the knee angle and the trunk to thigh angle measured during the standing-up motion. The processor may increase the first threshold value to a higher value if a rate of change in the trunk to thigh angle measured during the standing-up motion is higher than a rate of change in the knee angle measured during the standing-up motion.

If the rate of change in the trunk to thigh angle measured during the standing-up motion is higher than the rate of change in the knee angle measured during the standing-up motion, the user may be considered unstable in the standing-up motion. In such a case, the first threshold value is increased to a larger value. When the user stands up next time, the standing-up motion assistance starts at a timing that is determined using the changed first threshold value. In this way, the timing of starting the standing-up motion assistance is delayed. As a result, the user is assisted in the standing-up motion in a more stable way.

In accordance with another aspect of the disclosure, there is provided a standing-up assistance apparatus. The standing-up assistance apparatus includes a first sensor that measures a muscle potential of a lower leg of a user, a second sensor that measures a knee angle of the user, and a processor that determines whether starting to assist the user in a standing-up motion from a seated state is possible, based on, at least, the measured muscle potential and the measured knee angle, and outputs an instruction signal to an assistance mechanism that assists the user in the standing-up motion if the processor determines that starting to assist the user in the standing-up motion is possible.

In this way, the user is appropriately assisted in the standing-up motion, and is able to stand up in a stable way.

Embodiments of the disclosure are specifically described with reference to the drawings.

Each of the embodiments described below represents a general or specific example of the disclosure. Numerical values, shapes, elements, a layout position of the elements, a configuration of the elements, steps and the order of the steps in the embodiments are described for exemplary purposes only, and are not intended to limit the disclosure. Elements not described in independent claims indicative of a generic concept, from among the elements of the embodiments, may be any elements.

First Embodiment

Overview

FIG. 1A is a functional block diagram diagrammatically illustrating a standing-up assistance apparatus 10 of a first embodiment. Referring to FIG. 1A, the standing-up assistance apparatus 10 includes a first sensor 11, a third sensor 12a, a processor 15, and an assistance mechanism 17.

The first sensor 11 measures the muscle potential of a lower leg of a user. The third sensor 12a measures the trunk forward tilting angle of the user. The processor 15 determines whether starting to assist the user in the standing-up motion from a seated state is possible, based on the measured muscle potential and trunk forward tilting angle, and outputs an instruction signal if the processor 15 determines that starting to assist the user in the standing-up motion is possible. The assistance mechanism 17 starts assisting the user in the standing-up motion when the processor 15 outputs an instruction signal. The standing-up assistance apparatus 10 of the first embodiment includes the assistance mechanism 17. The standing-up assistance apparatus 10 may not necessarily have to include the assistance mechanism 17.

Figure 1B:
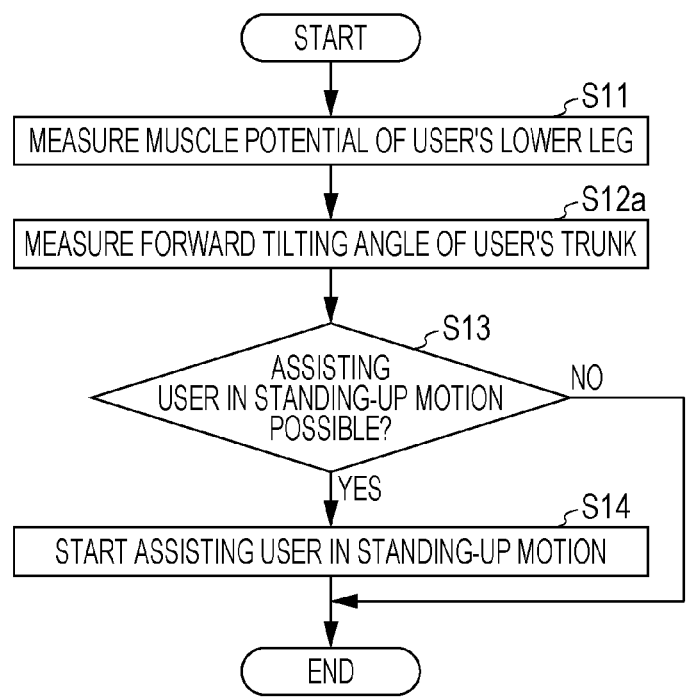
FIG. 1B is a flowchart diagrammatically illustrating a standing-up assistance method of the first embodiment.

FIG. 1B is a flowchart diagrammatically illustrating the standing-up assistance method of the first embodiment. In the standing-up assistance method, the first sensor 11 measures the muscle potential (value) of the user's lower leg (step S11), The third sensor 12a measures the user's trunk forward tilting angle (step S12a). Based on the measured muscle potential and trunk forward tilting angle, the processor 15 determines whether starting to assist the user in the standing-up motion from a seated state is possible (step S13). If the processor 15 determines that starting to assist the user in the standing-up motion is possible (yes branch from step S13), the assistance mechanism 17 starts assisting the user in the standing-up motion (step S14).

Since the processor 15 determines, based on the muscle potential value and trunk forward tilting angle of the user, whether starting to assist the user in the standing-up motion is possible, starting to assist the user in the standing-up motion may be started when the user's lower legs have a strong tension and the user tilts the trunk forward. This arrangement controls the fall of the user or the user's failure to stand up, and appropriately assists the user in the standing-up motion. The user may thus stand up in a stable way.

The standing-up assistance apparatus and the standing-up assistance method are described below in detail.

Configuration of Apparatus

Figure 2:
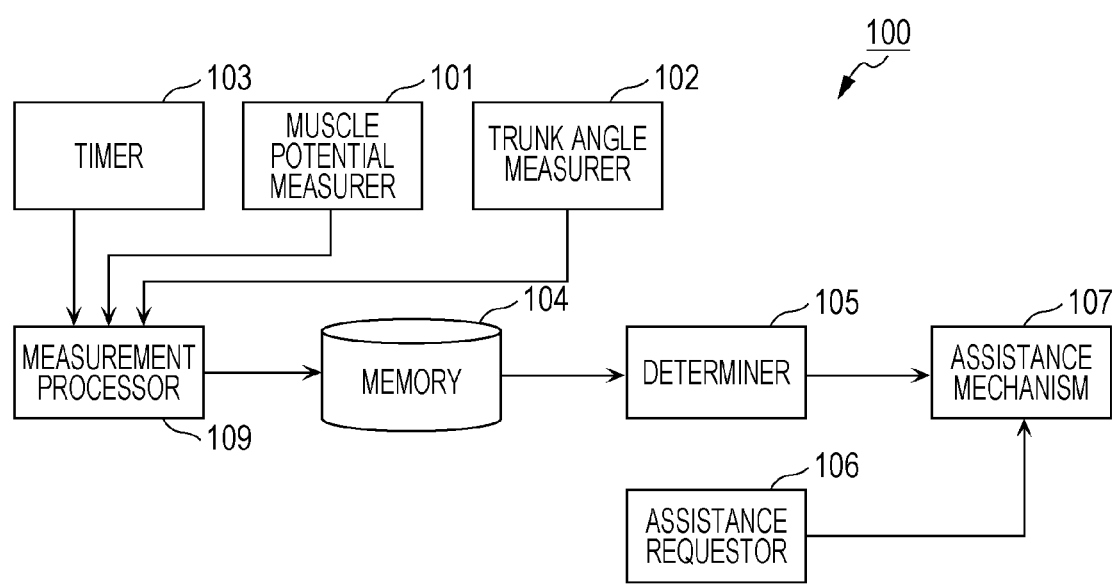
FIG. 2 is a functional block diagram specifically illustrating the standing-up assistance apparatus of the first embodiment.

FIG. 2 is a functional block diagram specifically illustrating a standing-up assistance apparatus 100 of the first embodiment. Referring to FIG. 2, the standing-up assistance apparatus 100 includes a muscle potential measurer 101, a trunk angle measurer 102, a timer 103, a memory 104, a determiner 105, a assistance requestor 106, an assistance mechanism 107, and a measurement processor 109. The standing-up assistance apparatus 100 of FIG. 2 is a more specific version of the standing-up assistance apparatus 10. The muscle potential measurer 101, the trunk angle measurer 102, and the determiner 105, illustrated in FIG. 2, correspond to the first sensor 11, the third sensor 12a, and the processor 15, illustrated in FIG. 1A, respectively. The assistance mechanism 107 of FIG. 2 corresponds to the assistance mechanism 17 of FIG. 1A.

Muscle Potential Measurer 101

The muscle potential measurer 101 measures the muscle potential value of the anterior tibial muscle as a muscle potential value of the lower leg. More specifically, the muscle potential measurer 101 measures the muscle potential value of the user's anterior tibial muscle using electrodes worn around a lower leg (more specifically, a lower thigh). The muscle potential value may be a value directly measured by the electrodes or a value that is calculated from the measured value. The muscle potential measurer 101 measures the muscle potential values of the anterior tibial muscles of the user's both legs.

Figure 3:
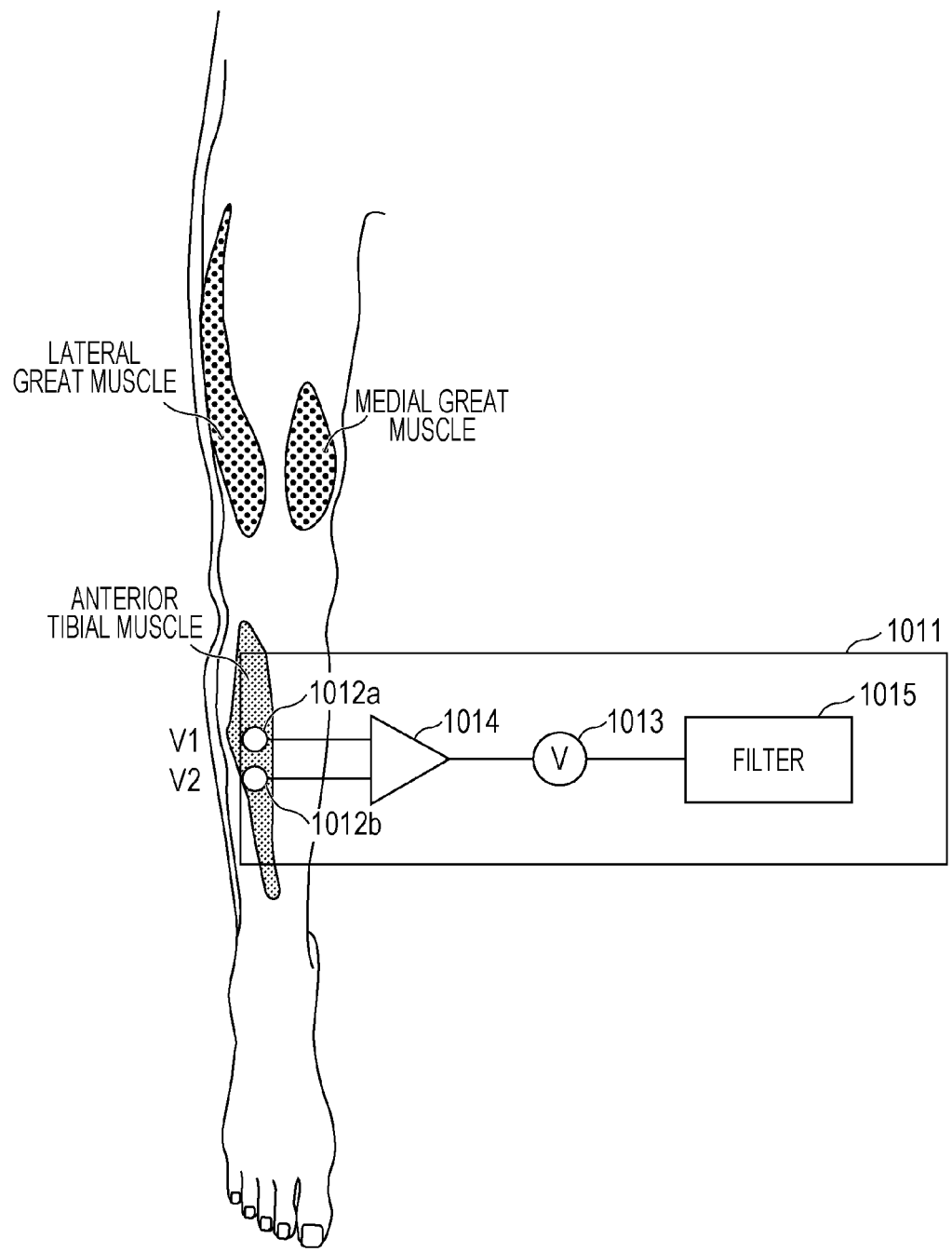
FIG. 3 illustrates an example of a muscle potential sensor included in a muscle potential measurer of the first embodiment.

FIG. 3 illustrates an example of a muscle potential sensor included in the muscle potential measurer 101 of the first embodiment. The muscle potential measurer 101 includes two muscle potential sensors 1011, and one muscle potential sensor 1011 measures the muscle potential value of the anterior tibial muscle of the user's right leg and the other muscle potential sensor 1011 measures the muscle potential value of the anterior tibial muscle of the user's left leg.

Referring to FIG. 3, the muscle potential sensor 1011 includes two electrodes 1012a and 1012b, an amplifier 1014, a rectifier 1013, and a filter 1015.

The electrodes 1012a and 1012b are secured to the skin on the user's anterior tibial muscles. The anterior tibial muscle is a muscle that is located at a shallow layer in the lower leg front. For example, the distance between the electrodes 1012a and 1012b may be from 10 mm to 30 mm.

The amplifier 1014 is a differential amplifier, for example. The amplifier 1014 amplifies a voltage difference between a voltage V1 measured using the electrode 1012a and a voltage V2 measured using the electrode 1012b, and outputs the amplified difference voltage as a measured voltage. The voltage V1 is a voltage difference between the ground and the electrode 1012a, and the voltage V2 is a voltage difference between the ground and the electrode 1012b.

The rectifier 1013 full-wave rectifies the measured voltage output from the amplifier 1014, thereby outputting the full-wave rectified measured voltage as a rectified voltage. The filter 1015 performs a low-pass filtering operation on the rectified voltage, thereby outputting the low-pass filter processed rectified voltage as a filter-processed voltage.

The muscle potential measurer 101 measures an average value, a maximum value, and a minimum value of the filter-processed voltages output from the two muscle potential sensors 1011 as the muscle potential values of the anterior tibial muscles.

Figure 4:
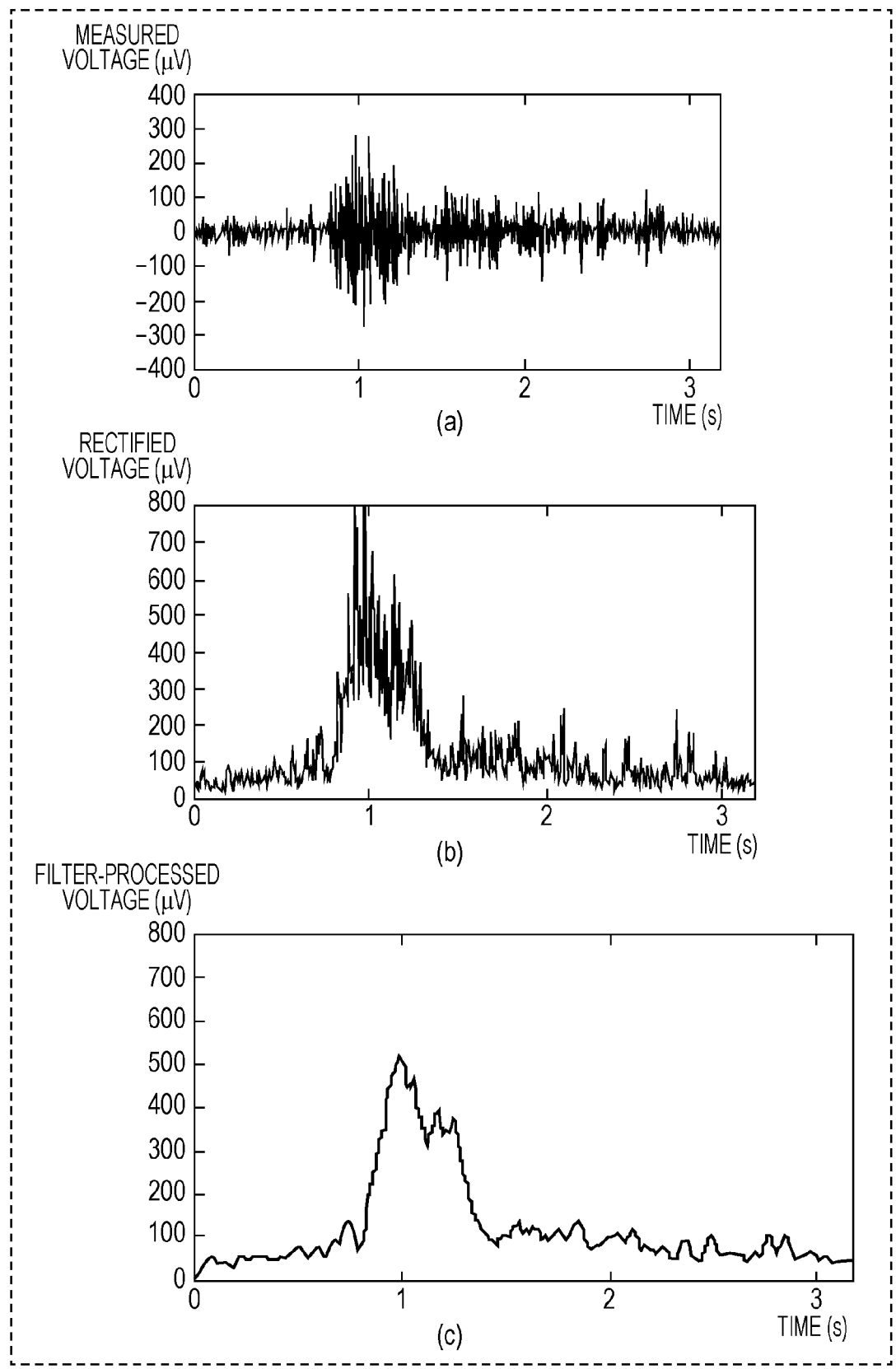
FIG. 4 illustrates examples of waveforms of a measured voltage output from an amplifier, a rectified voltage output from a rectifier, and a filter-processed voltage output from a filter in accordance with the first embodiment.

FIG. 4 illustrates examples of waveforms of a measured voltage output from the amplifier 1014, a rectified voltage output from the rectifier 1013, and a filter-processed voltage output from the filter 1015. Referring to FIG. 4, the ordinate represents voltage (μV) and the abscissa represents time (s).

The amplifier 1014 outputs a measured voltage having a waveform represented in FIG. 4(a). The rectifier 1013 full-wave rectifies the measured voltage having the waveform of FIG. 4(a). In order to obtain an envelope of the full-wave rectified waveform, the filter 1015 performs a low-pass filtering operation on the full-wave rectified waveform of FIG. 4(b) as illustrated in FIG. 4(c).

A frequency band that has undergone the low-pass filtering operation is a band equal to or below 2 Hz, for example. Through the low-pass filtering operation, a frequency component higher than 2 Hz contained in the rectified voltage is attenuated. The waveform resulting from performing the low-pass filtering operation on the rectified voltage is also referred to as an activity waveform of the anterior tibial muscle. A value of the activity waveform of the anterior tibial muscle at each time is referred to as an activity value of the anterior tibial muscle at the time.

The muscle potential value measured by the muscle potential measurer 101 may be values directly measured from the electrodes 1012a and 1012b or may be values corresponding to the measured values. The values corresponding to the measured values may be values that may be obtained by amplifying the directly measured values, by full-wave rectifying the measured values, or by performing the low-pass filtering operation on the measured values.

Trunk Angle Measurer 102

The trunk angle measurer 102 measures the trunk forward tilting angle of the upper half of the user's body.

Figure 5A:
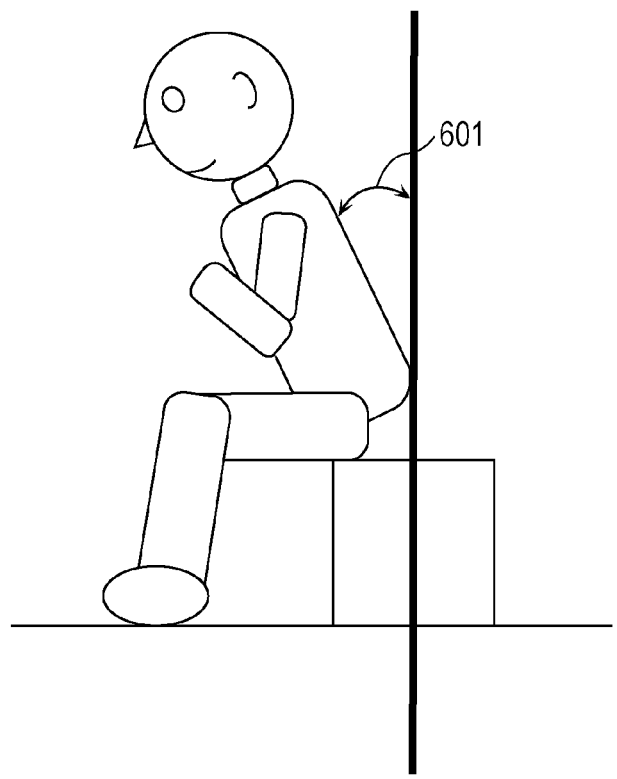
FIG. 5A illustrates an example of a trunk forward tilting angle of the upper half of the body of a user in accordance with the first embodiment.

FIG. 5A illustrates an example of the trunk forward tilting angle of the upper half of the user's body. The trunk forward tilting angle is an angle 601 made between a vertical direction and the user's trunk. More specifically, the trunk forward tilting angle is an angle between the vertical direction and the user's trunk, and becomes larger as the user tilts forward more. The user's trunk is the user's backbone, for example.

A hardware example of the trunk angle measurer 102 is a nine-axis sensor, for example. The nine-axis sensor includes an acceleration sensor, an angular velocity sensor, and a geomagnetic sensor. The acceleration sensor, the angular velocity sensor, and the geomagnetic sensor include an acceleration measuring circuit, an angular velocity measuring circuit, and a geomagnetic field measuring circuit, respectively. The nine-axis sensor may calculate an angle of the trunk with respect to the vertical direction as the trunk forward tilting angle. If only the acceleration sensor of the nine-axis sensor is used, the trunk forward tilting angle may be calculated by performing calibration on the acceleration sensor and accumulating the measured values of the acceleration sensor.

Figure 5B:
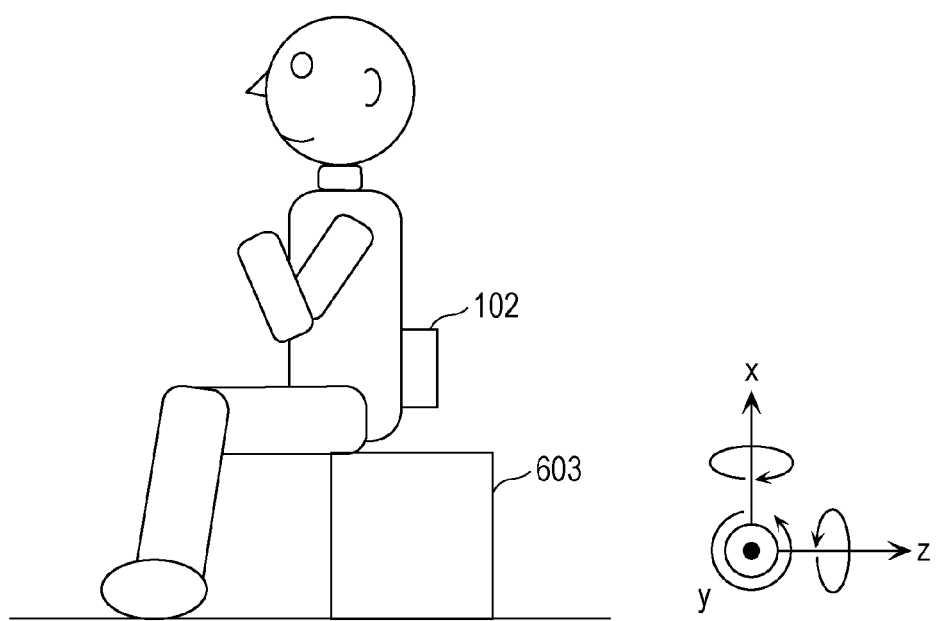
FIG. 5B illustrates an example of a state in which a trunk angle measurer of the first embodiment is worn on the user.

FIG. 5B illustrates an example of a state in which the trunk angle measurer 102 of the first embodiment is worn on the user. The trunk angle measurer 102 is worn on the waist of a user seated on a stool 603. The x axis, the y axis, and the z axis of the trunk angle measurer 102 are set up as illustrated in FIG. 5B. The x axis is aligned with the vertical direction, and the upward direction thereof is a positive direction. The y axis is perpendicular to the x axis, and aligned with the lateral direction of the user and the leftward direction thereof is a positive direction. The z axis is perpendicular to the x axis and aligned with the fore-aft direction of the user, and the backward direction thereof is a positive direction. The acceleration sensor measures acceleration of the trunk angle measurer 102 in each of the x axis, the y axis and the z axis. The geomagnetic sensor measures the geomagnetic field strength in each of the x axis, the y axis and the z axis. The angular velocity sensor measures an angular velocity of the trunk angle measurer 102 rotating around each of the x axis, the y axis and the z axis.

Figure 6:
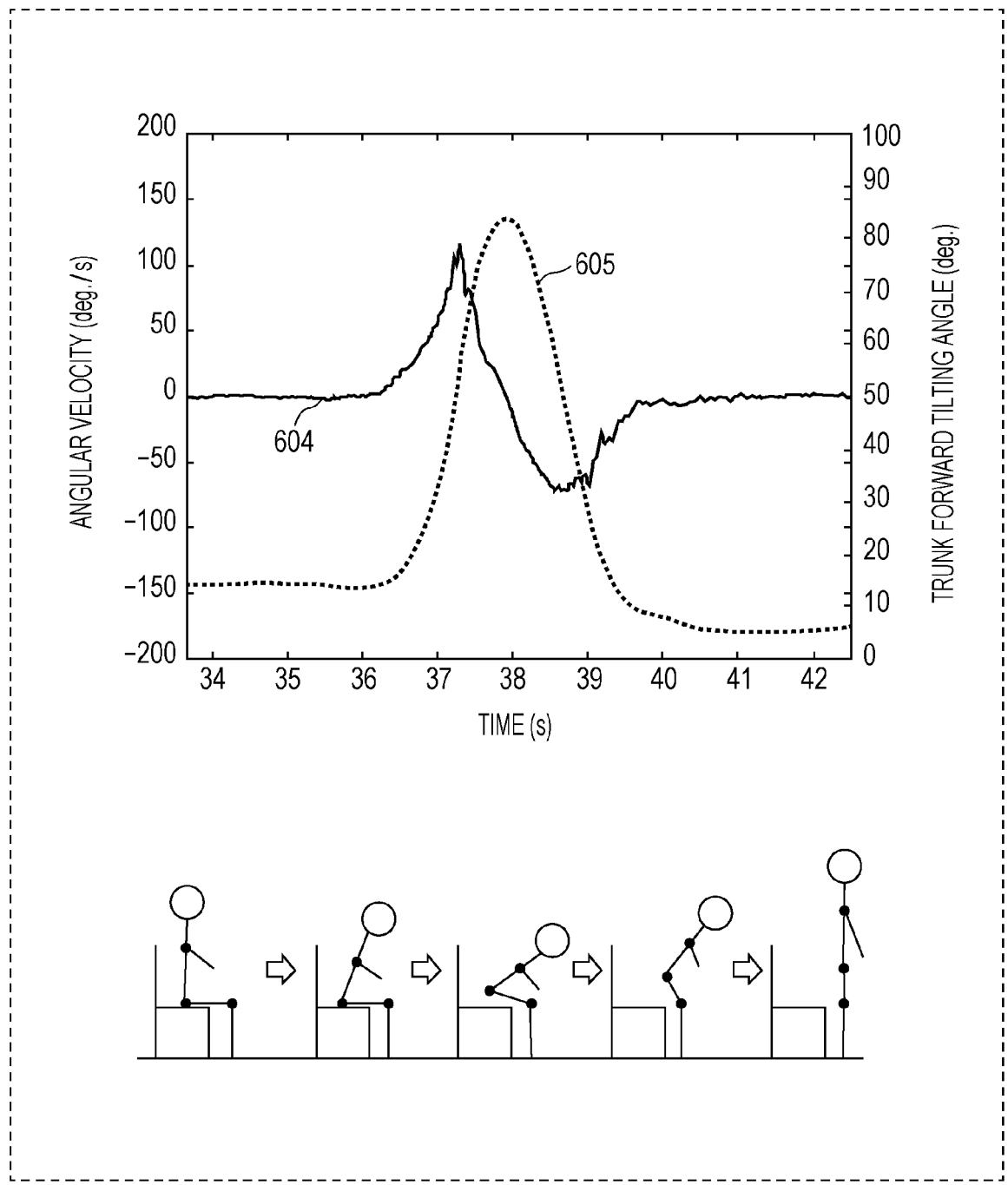
FIG. 6 illustrates angular velocity and trunk forward tilting angle measured by the trunk angle measurer of the first embodiment when the user is standing up.

FIG. 6 illustrates an angular velocity rotating around the y axis and trunk forward tilting angle measured by the trunk angle measurer 102 of the first embodiment when the user is standing up. A solid line in a graph of FIG. 6 represents an angular velocity 604 rotating about the y axis that is measured by the angular velocity sensor in the trunk angle measurer 102 when the user bends the user's upper body forward in the standing-up motion. A broken line in the graph of FIG. 6 represents a trunk forward tilting angle 605 that results from accumulating the measured angular velocities 604. Referring to FIG. 6, the trunk forward tilting angle 605 becomes larger as the user tilts forward and becomes smaller as the user returns to the user's original position after tilting forward.

The angular velocity sensor directly measures a change in the angular velocity, and calculates an angular velocity by integrating the change with the angular velocity measuring circuit. The trunk angle measurer 102 measures a trunk forward tilting angle that is obtained by adding to an initial angle an accumulated value of angular velocities measured the angular velocity sensor. The initial angle may be set through calibration, or may be stored in advance on an internal memory in the trunk angle measurer 102. Also, the trunk angle measurer 102 may correct a pre-stored initial angle through calibration. For example, the standing-up assistance apparatus 100 may instruct the user to wear the trunk angle measurer 102 along the x axis (in the vertical direction), and sets the trunk forward tilting angle measured by the trunk angle measurer 102 after the instruction to be the initial value (namely, zero deg.).

The trunk forward tilting angle measured by the trunk angle measurer 102 may be an angle calculated from a value directly measured by the nine-axis sensor, or may be an angle that is calculated from a value corresponding to the measured value. The value corresponding to the measured value may be obtained by amplifying, rectifying, or performing a filtering operation on the directly measured value.

Assistance Requestor 106

The assistance requestor 106 requests the assistance mechanism 107 to start assisting in the standing-up motion in response to a movement or an operation of the user. For example, the assistance requestor 106 requests the assistance to be started in response to an operation on a button or a voice-activated operation. More specifically, when the button on the standing-up assistance apparatus 100 is pressed by the user, the assistance requestor 106 requests the assistance mechanism 107 to start assisting in the standing-up motion. When the user speaks a keyword and a speech recognition circuit in the standing-up assistance apparatus 100 recognizes the keyword, the assistance requestor 106 requests the assistance mechanism 107 to start assisting in the standing-up motion.

Assistance Mechanism 107

The assistance mechanism 107 assists in the standing-up motion by assisting the user to extend the knees. Upon receiving the request to assist from the assistance requestor 106, the assistance mechanism 107 acquires current determination results from the determiner 105. If the determination results indicate that starting to assist in the standing-up motion is possible, the assistance mechanism 107 starts assisting the user in the standing-up motion. The determination results indicating that starting to assist in the standing-up motion is possible are output as the instruction signal to the assistance mechanism 107 from the determiner 105 that serves as a processor. The assistance mechanism 107, when receiving the instruction signal from the processor, starts to assist the user in the standing-up motion.

When the assistance mechanism 107 receives the instruction signal from the assistance requestor 106 as described above, the assistance mechanism 107 obtains the current determination results from the determiner 105. Alternatively, the assistance mechanism 107 may receive the current determination results continuously. If the current determination results indicate that starting to assist in the standing-up motion is possible, the assistance mechanism 107 starts assisting the user in the standing-up motion upon receiving the request to start assisting from the assistance requestor 106.

The assistance mechanism 107 may be a robot or a assist suit worn around the lower leg of the user, for example.

Figures 7, 8:
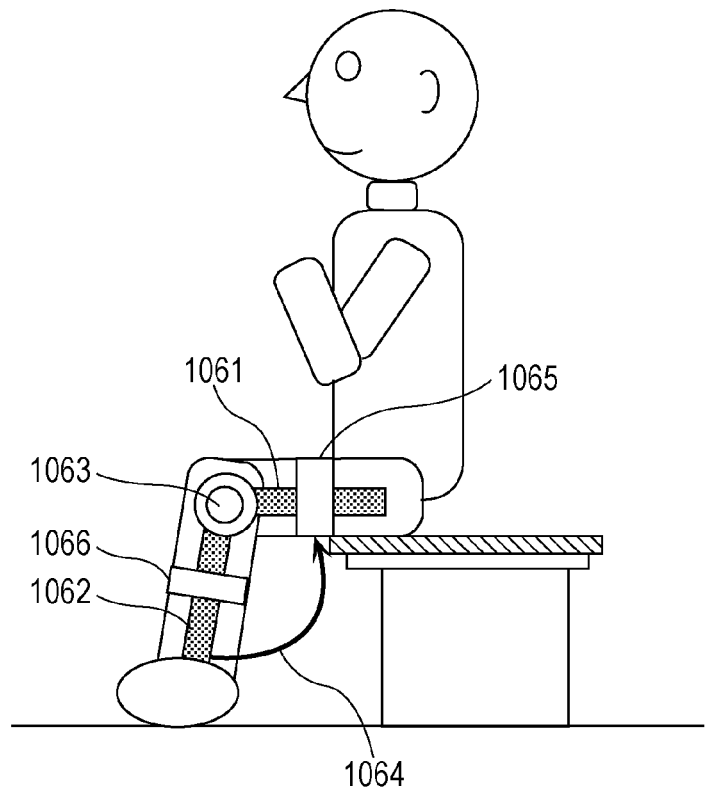
FIG. 7 illustrates an example of an assistance mechanism of the first embodiment.
FIG. 8 illustrates an example of information stored on a memory of the first embodiment.

FIG. 7 illustrates a configuration example of the assistance mechanism 107. Referring to FIG. 7, the assistance mechanism 107 includes an upper skeleton unit 1061, a lower skeleton unit 1062, and a moving unit 1063. The upper skeleton unit 1061 is pivotally connected at the moving unit 1063 with the lower skeleton unit 1062.

The upper skeleton unit 1061 is secured to the thigh of the user. The lower skeleton unit 1062 is secured to the foot or the lower leg of the user. The upper skeleton unit 1061 and the lower skeleton unit 1062, having fixtures 1065 and 1066, respectively, are secured to the user by the fixtures 1065 and 1066. The fixtures 1065 and 1066 may be tapes (hook and loop fasteners) or belts. Alternatively, the fixtures 1065 and 1066 may be strings. The moving unit 1063 may include a motor and a power source.

The thigh is part of the leg above the knee. The lower leg is part of the leg from the knee all the way down to the ankle.

As illustrated in FIG. 7, the moving unit 1063 moves the upper skeleton unit 1061 in a direction to extend the knee of the user (in the direction labeled with an arrow mark 1064) about a location between the upper skeleton unit 1061 and the lower skeleton unit 1062 (or at the knee). In this way, the user is assisted in the standing-up motion.

If the assistance mechanism 107 is the cloth assist suit worn by the user, each of the upper skeleton unit 1061 and the lower skeleton unit 1062 may be wrapped up in cloth.

Timer 103

The timer 103 measures present time, and then outputs a time signal indicating the measured present time to the measurement processor 109. For example, every 0.01 s, the timer 103 outputs the time signal indicating the present time.

Memory 104

The memory 104 is a storage medium having a storage region that stores the muscle potential value of the anterior tibial muscle and the trunk forward tilting angle, and may be a hard disk or a memory.

Measurement Processor 109

The measurement processor 109 acquires time represented by the time information output by the timer 103, the muscle potential value of the anterior tibial muscle measured by the muscle potential measurer 101 at the time, and the trunk forward tilting angle measured by the trunk angle measurer 102 at the time. The measurement processor 109 stores on the memory 104 the time, the muscle potential value, and the trunk forward tilting angle in association with each other.

FIG. 8 illustrates an example of information stored on the memory 104.

The measurement processor 109 stores the time "13:45: 30.00" represented by the time information, the muscle potential value of the anterior tibial muscle "0.000639 V" at the time, and the trunk forward tilting angle "18.32 deg." at the time in association with each other on the memory 104. Alternatively, the measurement processor 109 may store the time, the muscle potential value, the trunk forward tilting angle in association with each other every 0.01 s on the memory 104. Alternatively, the measurement processor 109 may acquire a user identity (ID) that is identification information of the user, and stores the user ID, the time, the muscle potential value, and the trunk forward tilting angle in association with each other on the memory 104. If a muscle potential value of a medial great muscle is measured, the measurement processor 109 may store on the memory 104 the time at which the muscle potential value is measured and the muscle potential value of the medial great muscle in association with each other.

FIG. 9A and FIG. 9B illustrate other examples of information stored on the memory 104.

The timer 103 may output a clock signal instead of outputting the time signal as described above. In such a case, the measurement processor 109 calculates time at which a first time interval (0.001 s, for example) elapses in response to the clock signal, and acquires the muscle potential value of the anterior tibial muscle measured at the time from the muscle potential measurer 101. Referring to FIG. 9A, the measurement processor 109 stores the order of acquisition of the muscle potential value, the muscle potential value, and the time that is calculated when the muscle potential value is acquired, in association with each other, on the memory 104. For example, the measurement processor 109 stores an order of acquisition "1", a muscle potential value acquired for the first time, and reference time (0 s, for example) in association with each other on the memory 104. The measurement processor 109 stores an order of acquisition "2", a muscle potential value acquired for the second time, and time "reference time+first time interval" (s) in association with each other on the memory 104. The measurement processor 109 stores an order of acquisition "3", a muscle potential value acquired for the third time, and time "reference time+first time interval×2" (s) in association with each other on the memory 104. In this way, the measurement processor 109 stores an order of acquisition "n", a muscle potential value acquired for the n-th time, and time "reference time+first time interval×(n−1)" (s) in association with each other on the memory 104 (n is a natural number).

Similarly, the measurement processor 109 calculates time at which a second time interval (0.01 s, for example) elapses in response to the clock signal, and acquires the trunk forward tilting angle measured at the time from the trunk angle measurer 102. Referring to FIG. 9B, the measurement processor 109 store the order of acquisition of the trunk forward tilting angle, the trunk forward tilting angle, and the time that is calculated when the trunk forward tilting angle is acquired, in association with each other, on the memory 104. For example, the measurement processor 109 stores an order of acquisition "1", a trunk forward tilting angle first, and reference time (0 s, for example) in association with each other on the memory 104. The measurement processor 109 stores an order of acquisition "2", a trunk forward tilting angle acquired for the second time, and time "reference time+second time interval" (s) in association with each other on the memory 104. The measurement processor 109 stores an order of acquisition "3", a trunk forward tilting angle acquired for the third time, and time "reference time+second time interval×2" (s) in association with each other on the memory 104. In this way, the measurement processor 109 stores an order of acquisition "n", a trunk forward tilting angle acquired for the n-th time, and time "reference time+ second time interval×(n−1)" (s) in association with each other on the memory 104 (n is a natural number). The first time interval and the second time interval may or may not be equal to each other.

Determiner 105

Based on the muscle potential value of the anterior tibial muscle of the user and the trunk forward tilting angle of the upper half of the user's body, the determiner 105 determines whether the user is in a state that allows the user to be assisted in the standing-up motion. In other words, the determiner 105 determines whether starting to assist the user in the standing-up motion is possible, using the muscle potential value of the anterior tibial muscle of the user and the trunk forward tilting angle of the user. More specifically, the determiner 105 determines that starting to assist the user in the standing-up motion is possible if the first condition that the measured muscle potential value is equal to or higher than the first threshold value and the third condition that the measured trunk forward tilting angle is equal to or larger than the third threshold value are concurrently satisfied. In other words, if (i) the muscle potential value is the first threshold value or higher and (ii) the trunk forward tilting angle is the third threshold value or larger, the determiner 105 determines that starting to assist the user in the standing-up motion is possible. The determiner 105 may pre-store the first threshold value and the third threshold value, or may read the first threshold value and the third threshold value from an external storage medium.

The muscle potential value and trunk forward tilting angle to be used in the determination may be a muscle potential value and trunk forward tilting angle associated with the latest time stored on the memory 104. The determiner 105 references the memory 104 each time a muscle potential value and trunk forward tilting angle associated with the latest time are stored on the memory 104, and thus identifies the latest muscle potential value and trunk forward tilting angle. Based on the latest muscle potential value and trunk forward tilting angle thus identified, the determiner 105 determines whether starting to assist the user in the standing-up motion is possible at the current time point.

Figure 10A:
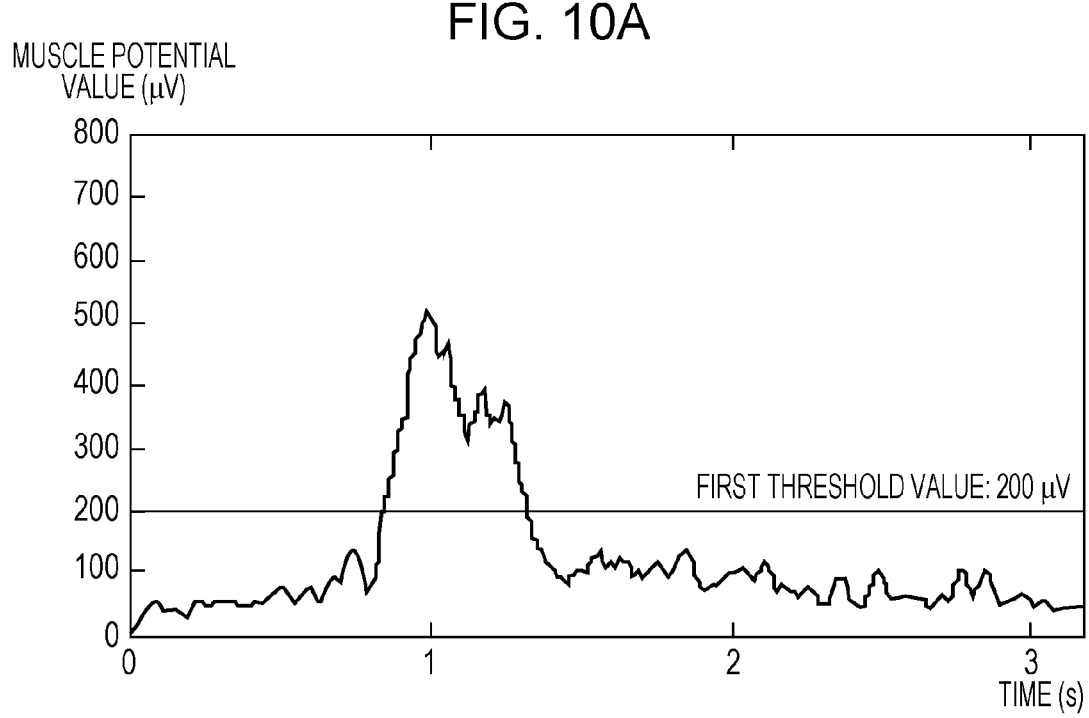
FIG. 10A illustrates an example of a waveform of a muscle potential value of an anterior tibial muscle and a first threshold value in accordance with the first embodiment.
Figure 10B:
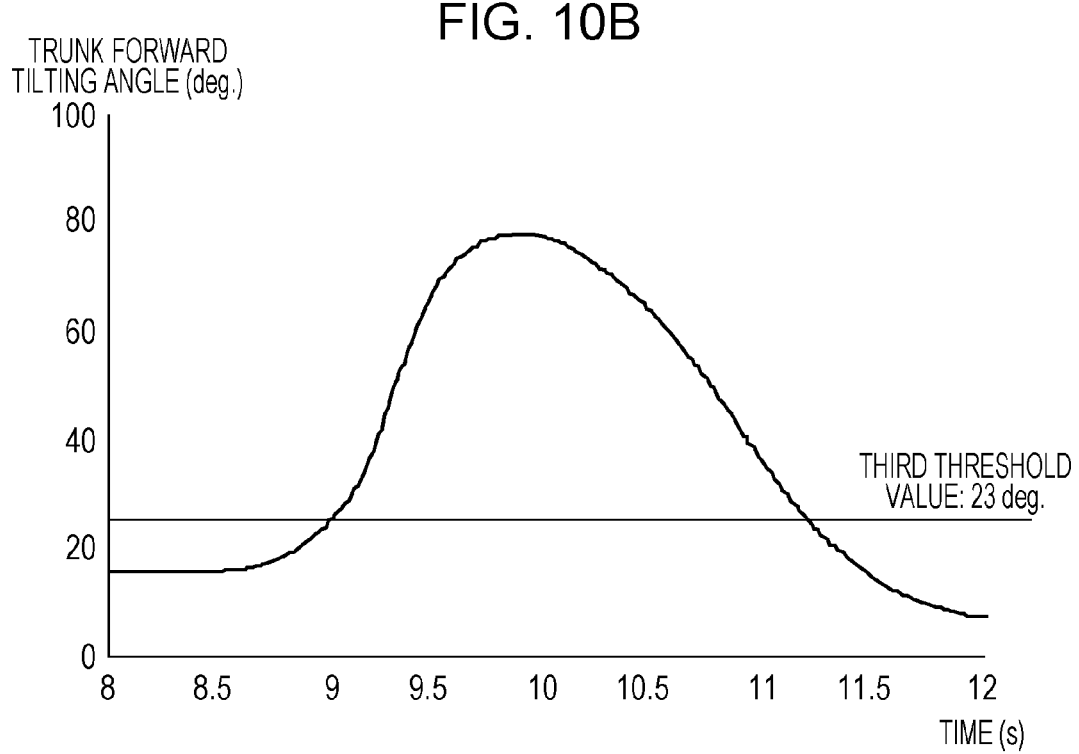
FIG. 10B illustrates an example of a waveform of the trunk forward tilting angle and a third threshold value in accordance with the first embodiment.

FIG. 10A illustrates an example of the waveform of the muscle potential value of an anterior tibial muscle and the first threshold value, and FIG. 10B illustrates an example of the waveform of the trunk forward tilting angle and the third threshold value.

Referring to FIG. 10A, the determiner 105 determines whether the muscle potential value of the user's anterior tibial muscle is the first threshold value (200 μV) or higher, Referring to FIG. 10B, the determiner 105 further determines whether the user's trunk forward tilting angle is the third threshold value (23 deg., for example) or larger. If the muscle potential value is the first threshold value or higher and the trunk forward tilting angle is the third threshold value or larger, the determiner 105 determines that starting to assist the user in the standing-up motion is possible. The determiner 105 outputs the instruction signal to the assistance mechanism 107.

Without referencing the information stored on the memory 104, the determiner 105 may directly acquire the muscle potential value of the user's anterior tibial muscle and the user's trunk forward tilting angle respectively from the muscle potential measurer 101 and the trunk angle measurer 102. The determiner 105 may acquire from the muscle potential measurer 101 and the trunk angle measurer 102 the times when the muscle potential value and the trunk forward tilting angle are measured. The determiner 105 may store the first time interval and the second time interval on an internal memory thereof. In this case, using the first time interval and the second time interval, the determiner 105 calculates time at which the muscle potential value of the user's anterior tibial muscle and the trunk forward tilting angle of the upper half of the user's body are to be acquired. In response to the clock signal from the timer 103, the determiner 105 acquires the muscle potential value and trunk forward tilting angle at the calculated time, and determines whether starting to assist in the standing-up motion is possible at the current time point, based on the latest muscle potential value and trunk forward tilting angle acquired.

Process of Standing-Up Assistance Apparatus 100

Figure 11A:
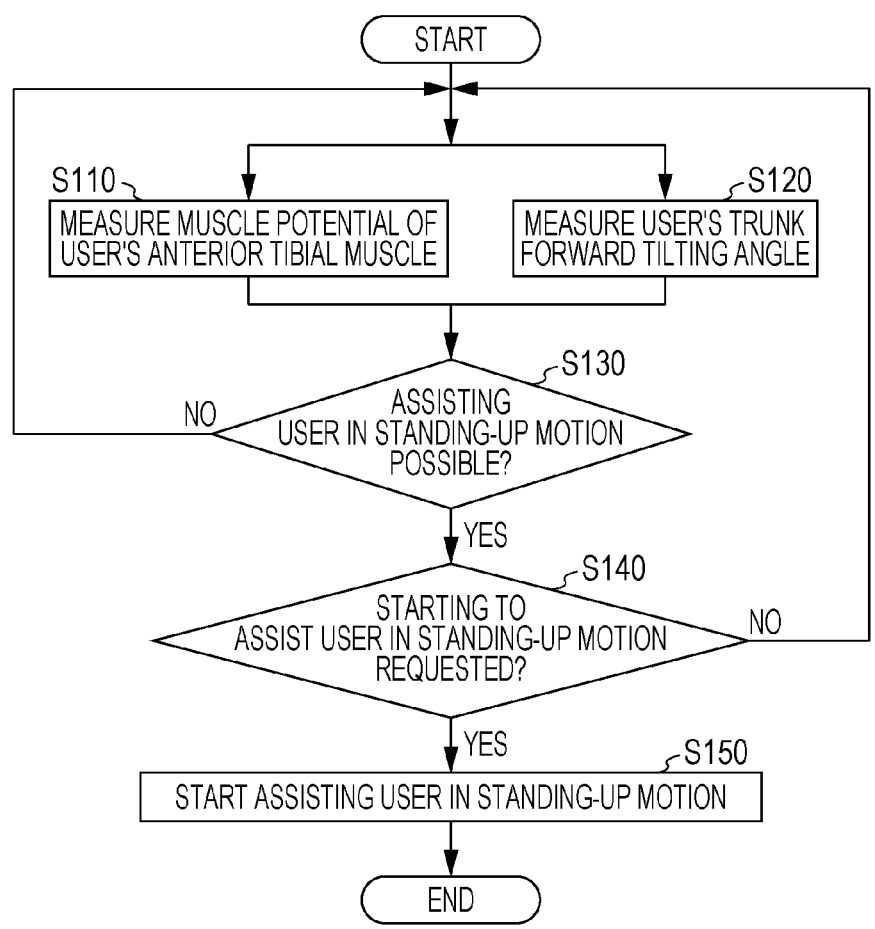
FIG. 11A is a flowchart illustrating a process of the standing-up assistance apparatus of the first embodiment.

FIG. 11A is a flowchart illustrating a process of the standing-up assistance apparatus 100.
Step S110
The muscle potential measurer 101 measures the muscle potential value of the user's anterior tibial muscle. The muscle potential value to be measured is a value obtained from the muscle potential values of the anterior tibial muscles of the user's both legs (such as an average value, a minimum value, or a maximum value thereof).
Step S120
The trunk angle measurer 102 measures the user's trunk forward tilting angle.
Step S130
Based on the muscle potential value of the anterior tibial muscle measured in step S110 and the trunk forward tilting angle measured in step S120, the determiner 105 determines whether starting to assist in the standing-up motion is possible. If the determiner 105 determines that starting to assist in the standing-up motion is possible, the standing-up assistance apparatus 100 proceeds to step S140. If the determiner 105 determines that starting to assist in the standing-up motion is not possible, the standing-up assistance apparatus 100 returns to the operations in steps S110 and S120.
Step S140
The assistance mechanism 107 verifies whether a request to start assisting in the standing-up motion has been received from the assistance requester 106. If the request to start assisting in the standing-up motion has been received, the standing-up assistance apparatus 100 proceeds to step S150. If the request to start assisting in the standing-up motion has not been received, the standing-up assistance apparatus 100 returns to the operations in steps S110 and S120.
Step S150
The assistance mechanism 107 starts assisting the user in the standing-up motion.

Detailed Process of Determiner 105

Figure 11B:
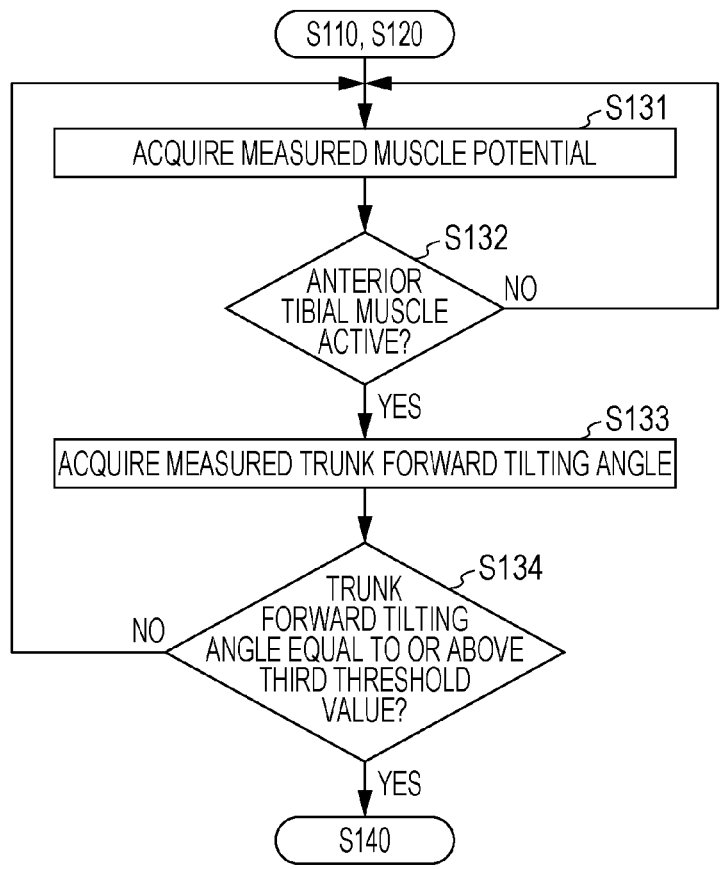
FIG. 11B is a flowchart illustrating the detail process of step S130 of FIG. 11A.

FIG. 11B is a flowchart illustrating the detail process of step S130 of FIG. 11A.
Step S131
The determiner 105 acquires the muscle potential value of the anterior tibial muscle from the memory 104.
Step S132
The determiner 105 determines whether the muscle potential value of the anterior tibial muscle acquired in step S131 is the first threshold value or higher. The muscle potential value of the anterior tibial muscle being the first threshold value or higher indicates that the anterior tibial muscle is active.

If the muscle potential value of the anterior tibial muscle acquired in step S131 is the first threshold value or higher, the determiner 105 proceeds to step S133. If the determiner 105 determines that the muscle potential value of the anterior tibial muscle is lower than the first threshold value, the determiner 105 returns to the operation in step S131. After returning to step S131, the determiner 105 acquires a new muscle potential value of the anterior tibial muscle.

The determiner 105 may determine whether the anterior tibial muscle is active, using an amount of change in the muscle potential value of the anterior tibial muscle rather than using the muscle potential value of the anterior tibial muscle. For example, the determiner 105 may detect an amount of change in the muscle potential value of the anterior tibial muscle equal to or higher than a threshold value, and may set, to be tb, time when the used muscle potential value is measured, and store tb on the memory 104. If an amount of change (Ib−Ia) in the muscle potential value of the anterior tibial muscle is the threshold value or higher, the time when the muscle potential value Ib is measured is set to be tb. If time ta is earlier than tb (ta<tb), the muscle potential value measured at time ta is set to be Ia, and the muscle potential value measured at time tb is set to be Ib. If the amount of change is the threshold value or higher, the relationship Ib>Ia holds.

Step S133

The determiner 105 acquires the trunk forward tilting angle from the memory 104.

Step S134

The determiner 105 determines whether the trunk forward tilting angle acquired in step S133 is the third threshold value or larger. If the determiner 105 determines that the trunk forward tilting angle acquired in step S133 is the third threshold value or larger, the standing-up assistance apparatus 100 proceeds to an operation in step S140. If the determiner 105 determines that the trunk forward tilting angle acquired in step S133 is smaller than the third threshold value, the standing-up assistance apparatus 100 returns to the operation in step S131. When the determiner 105 returns to the operation in step S131, and then reaches the operation in step S133 again, the determiner 105 acquires a new muscle potential value and a new trunk forward tilting angle. Alternatively, the determiner 105 may determine whether an amount of change in the trunk forward tilting angle, rather than the trunk forward tilting angle itself, is a threshold value or larger.

Effect

In accordance with the first embodiment, a determination is made as to whether starting to assist the user in the standing-up motion is possible, based on the muscle potential value of the lower leg of the user and the user's trunk forward tilting angle. The assistance in the standing-up motion may be started if the user has a strong tension in the lower leg and tilts the trunk forward. This arrangement controls the occurrence of the fall of the user or failure to stand up. The user is thus appropriately assisted in the standing-up motion, and the user may stand up in a stable way.

In accordance with the first embodiment, starts assisting the user in the standing-up motion is determined to be possible if the measured muscle potential value is the first threshold value or higher and the measured trunk forward tilting angle is the third threshold value or larger. The standing-up motion assistance is appropriately started at the timing when the user has a strong tension in the lower leg, and the user tilts forward the upper half of the user's body. The user may thus stand up in a stable way.

Second Embodiment

The standing-up assistance apparatus of the first embodiment calculates the muscle potential value of the user's lower leg and the user's trunk forward tilting angle to determine whether starting the standing-up motion assistance is possible. In accordance with a standing-up assistance apparatus 10 of a second embodiment, the user's knee angle is measured instead of the trunk forward tilting angle. The knee angle is a knee joint angle.

Overview

Figure 12A:
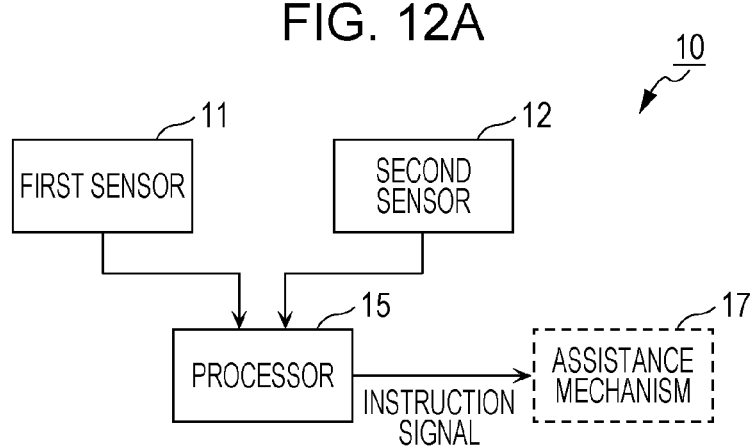
FIG. 12A is a functional block diagram diagrammatically illustrating a standing-up assistance apparatus of a second embodiment.

FIG. 12A is a functional block diagram diagrammatically illustrating the standing-up assistance apparatus 10 of the second embodiment. As illustrated in FIG. 12A, the standing-up assistance apparatus 10 includes a first sensor 11, a second sensor 12, a processor 15, and an assistance mechanism 17.

The first sensor 11 measures the muscle potential value of the user's lower leg. The second sensor 12 measures the user's knee angle. Based on the measured muscle potential value and knee angle, the processor 15 determines whether starting to assist the user in the standing-up motion from a seated state is possible. Upon determining that starting to assist the user the standing-up motion is possible, the processor 15 outputs an instruction signal. When the processor 15 outputs the instruction signal, the assistance mechanism 17 starts assisting the user in the standing-up motion. The standing-up assistance apparatus 10 of the second embodiment includes the assistance mechanism 17. The standing-up assistance apparatus 10 may not necessarily have to include the assistance mechanism 17.

Figure 12B:
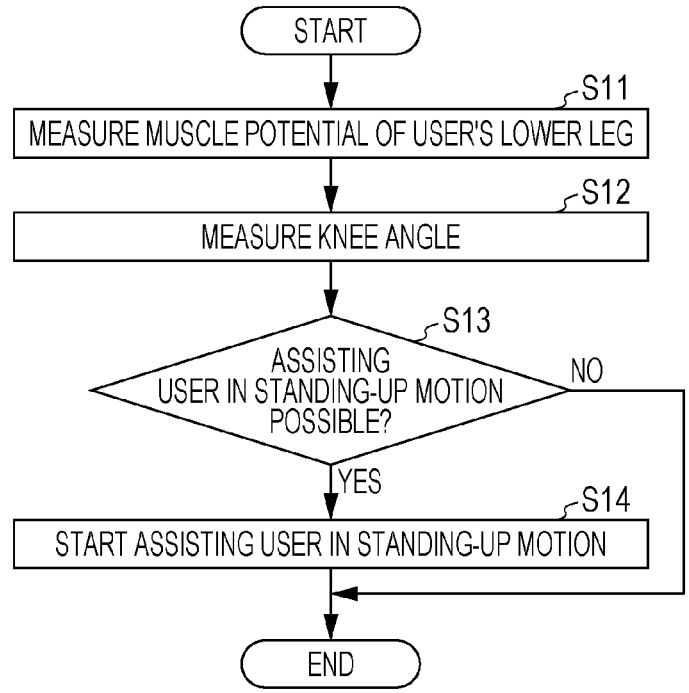
FIG. 12B is a flowchart diagrammatically illustrating a standing-up assistance method of the second embodiment.

FIG. 12B is a flowchart diagrammatically illustrating a standing-up assistance method of the second embodiment. In starting to assist in the standing-up motion, the first sensor 11 measures the muscle potential value of the user's lower leg (step S11). The second sensor 12 measures the user's knee angle (step S12). Based on the measured the muscle potential value and knee angle, the processor 15 determines whether starting to assist the user in the standing-up motion from a seated state is possible (step S13). If the processor 15 determines that starting to assist the user in the standing-up motion is possible (yes branch from step S13), the assistance mechanism 17 starts assisting the user in the standing-up motion (step S14).

Since a determination is made as to whether starting to assist the user in the standing-up motion is possible, based on the user's knee angle and the muscle potential value of the user's lower leg, the assistance in the standing-up motion may be started when the user appropriately bends the knees and has a strong tension in the lower legs. This arrangement controls a failure to stand up and appropriately assists the user in the standing-up motion. The user may thus stand up in a stable way.

As in the first embodiment, the first sensor 11 measures the muscle potential value of the anterior tibial muscle as the muscle potential value of the lower leg. The assistance mechanism 17 then assists in the standing-up motion by assisting the user in extending the knee.

More specifically, the processor 105 determines that starting to assist the user in the standing-up motion is possible if the first condition that the measured muscle potential value is the first threshold value or higher and the second condition that the measured knee angle is a second threshold value or smaller are concurrently satisfied. The second threshold value is 60° or larger and 100° or smaller. The user's knee angle measured by the second sensor 12 is the knee angle of the user's left knee or the knee angle of the user's right knee, whichever is smaller.

First Modification

As in the first embodiment, the standing-up assistance apparatus 10 may further include the third sensor 12a that measures the user's trunk forward tilting angle. In such a case, the processor 15 determines whether starting to assist in the standing-up motion is possible, based on the measured muscle potential value, the knee angle, and the trunk forward tilting angle.

The first modification is different from the first embodiment in that the first threshold value of the muscle potential value used to determine whether the anterior tibial muscle is active is changed in response to the user's knee angle.

Configuration of Apparatus

Figure 13:
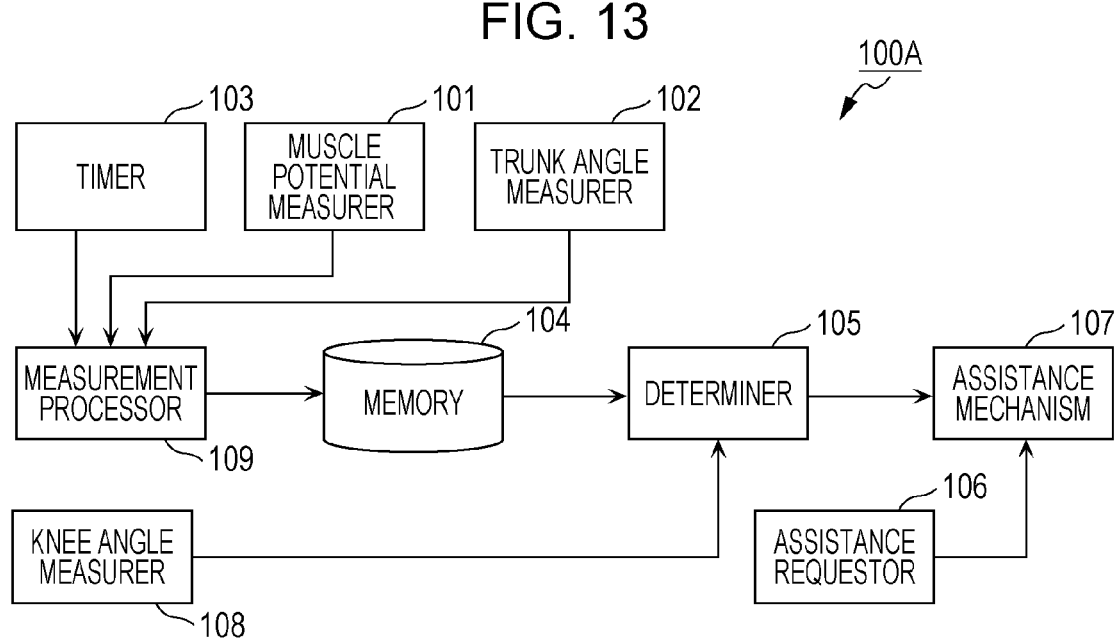
FIG. 13 is a functional block diagram of the standing-up assistance apparatus of a first modification of the second embodiment.

FIG. 13 is a functional block diagram of a standing-up assistance apparatus 100A of a first modification of the second embodiment. The standing-up assistance apparatus 100A of the first modification includes the elements of the standing-up assistance apparatus 100 of FIG. 2 and a knee angle measurer 108 to measure the knee angle as well.

Knee Angle Measurer 108

The knee angle measurer 108 is the second sensor that measures the user's knee angle, and may include an encoder, for example.

Figure 14:
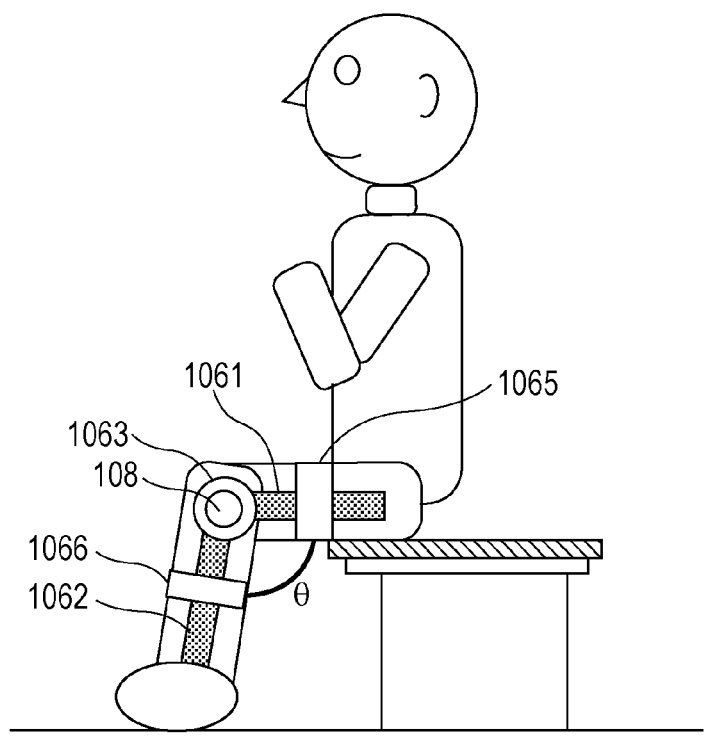
FIG. 14 illustrates an example of a location of a knee angle measurer and a knee angle in accordance with the first modification of the second embodiment.

FIG. 14 illustrates an example of the location of the knee angle measurer 108 and the knee angle.

The knee angle measurer 108 that may include an encoder, for example, is mounted in the moving unit 1063 having a motor as illustrated in FIG. 14, and measures an angle of rotation of the motor of the moving unit 1063. From the angle of rotation of the motor, the knee angle measurer 108 calculates a knee angle θ made between the upper skeleton unit 1061 and the lower skeleton unit 1062. In this way, the knee angle θ is calculated.

FIG. 15A illustrates an operation example in which the user breaks the balance of the body when assistance starts in a standing-up motion, and FIG. 15B illustrates a failure example of the standing-up motion.

If the assistance in the standing-up motion starts with the knee angle being larger as illustrated in FIG. 15A, the user could break the balance of the body and fall. If the assistance in the standing-up motion starts with the knee angle being larger as illustrated in FIG. 15B, the user could extend the knees in a seated state without being unable to stand up. The standing-up assistance apparatus 100A of the first modification determines whether the assistance in the standing-up motion is possible, using the knee angle measured by the knee angle measurer 108. In this way, a risk of fall may be reduced.

An experiment conducted to determine a relationship between the knee angle and the muscle potential value is described below.

Figure 16:
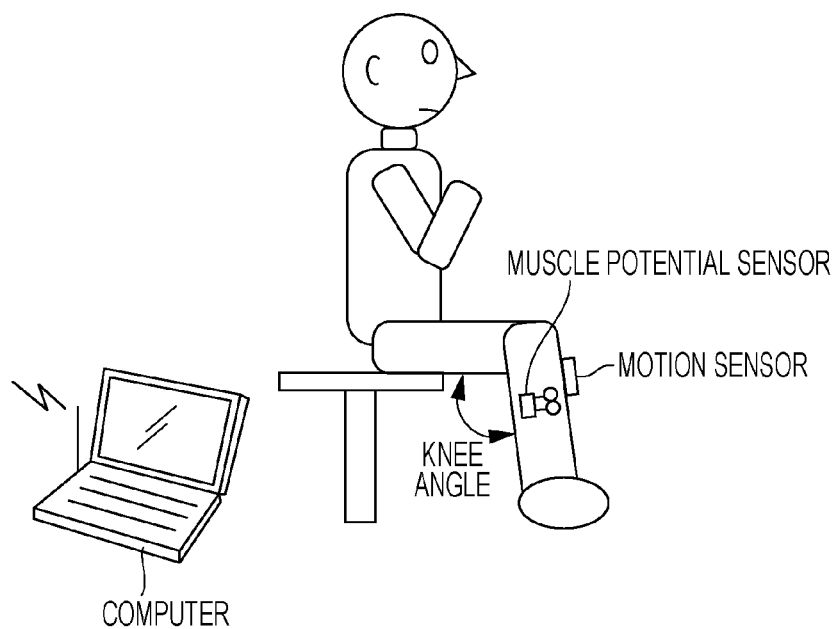
FIG. 16 illustrates an example of an experiment.

FIG. 16 illustrates an example of the experiment. In the experiment as illustrated in FIG. 16, an amount of muscular activity of the anterior tibial muscle was measured using a muscle potential sensor and a motion sensor secured to the user's lower leg when the knee angle was varied immediately prior to the standing-up motion. The amount of muscular activity corresponds to the muscle potential value.

Figure 17:
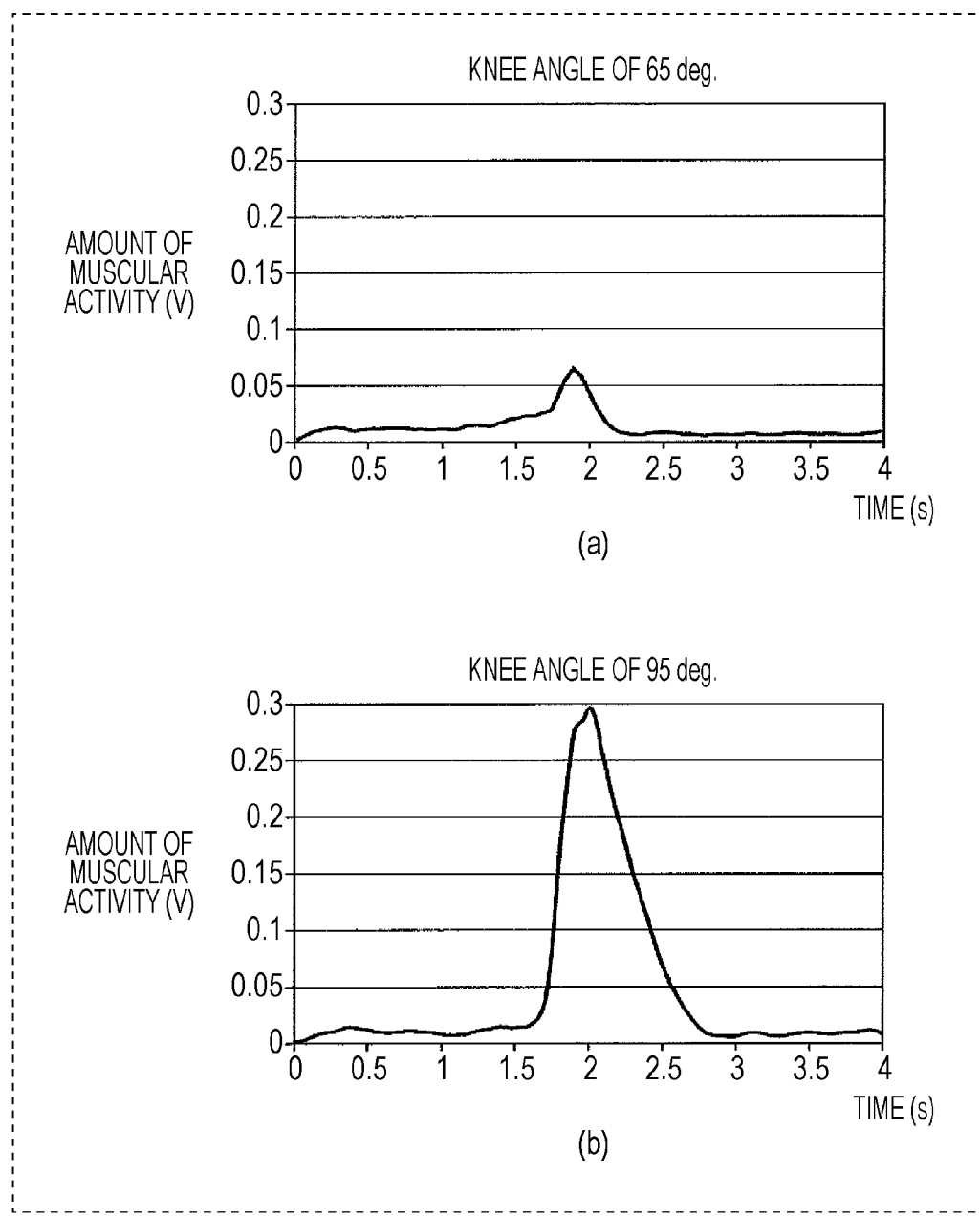
FIG. 17 illustrates an example of measurement results of an amount of muscular activity in the standing-up motion when the knee angle is 65° or 95° immediately prior to the standing-up motion.

FIG. 17 illustrates an example of measurement results of an amount of muscular activity in the standing-up motion when the knee angle is 65° or 95° immediately prior to the standing-up motion.

As illustrated in FIG. 17(a) and FIG. 17(b), the amount of muscular activity involved in the standing-up motion is smaller when the user stands up with the knee angle being at 65° immediately prior to the standing-up motion than when the user stands up with the knee angle being at 95° immediately prior to the standing-up motion. More specifically, a maximum value of the amount of muscular activity at a knee angle of 65° is about 0.06 V while a maximum value of the amount of muscular activity at a knee angle of 95° is about 0.3 V.

Figure 18:
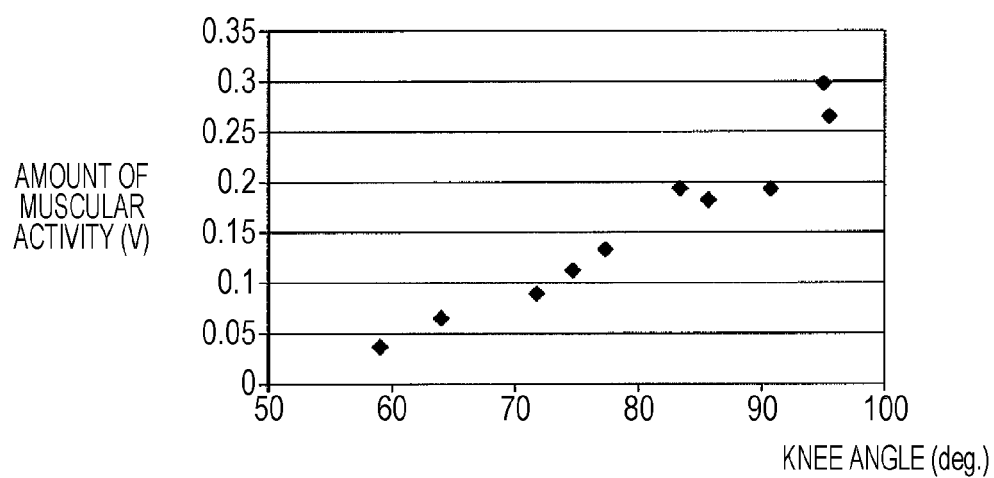
FIG. 18 illustrates a maximum value of the amount of muscular activity of the anterior tibial muscle when the standing-up motion is performed at each of multiple knee angles.

FIG. 18 illustrates a maximum value of the amount of muscular activity of the anterior tibial muscle when the standing-up motion is performed at each of multiple knee angles. Referring to FIG. 18, the maximum value of the amount of muscular activity involved in the standing-up motion becomes larger as the knee angle increases.

With the first threshold value of the muscle potential value, the assistance in the standing-up motion may be correctly determined at a given knee angle, while the assistance in the standing-up motion may not be correctly determined at another knee angle. More specifically, as illustrated in FIG. 18, the first threshold value may be set to be 0.15 V when the knee angle and the amount of muscular activity are related as illustrated in FIG. 18. In such a case, if the standing-up motion is activated with the knee angle being smaller than 80°, the muscle potential value is below 0.15 V, and the assistance in the standing-up motion is not determined to be possible. On the other hand, the first threshold value may be set to be 0.04 V. Starting to assist in the standing-up motion is determined to be possible with the user having a larger knee angle even if the user has no intention to stand up or is not in a state ready to stand up. As a result, the user may run the risk of fall depending on the knee angle. In accordance with the first modification, the first threshold value is modified depending on the knee angle.

The knee angle measured by the knee angle measurer 108 may be an angle that is directly calculated from a measured value or may be angle that is calculated from a value corresponding to the measured value. The value corresponding to the measured value may be obtained by amplifying, rectifying or performing a filtering operation on the directly measured value.

Determiner 105

The determiner 105 of the first modification modifies the first threshold value in response to the knee angle measured by the knee angle measurer 108. More specifically, the determiner 105 sets the first threshold value to be lower as the measured knee angle is smaller. If the first condition that the measured muscle potential value is the first threshold value or higher and the third condition that the measured trunk forward tilting angle is the third threshold value or larger are concurrently satisfied, the determiner 105 determines that starting to assist the user in the standing-up motion is possible.

Figure 19:
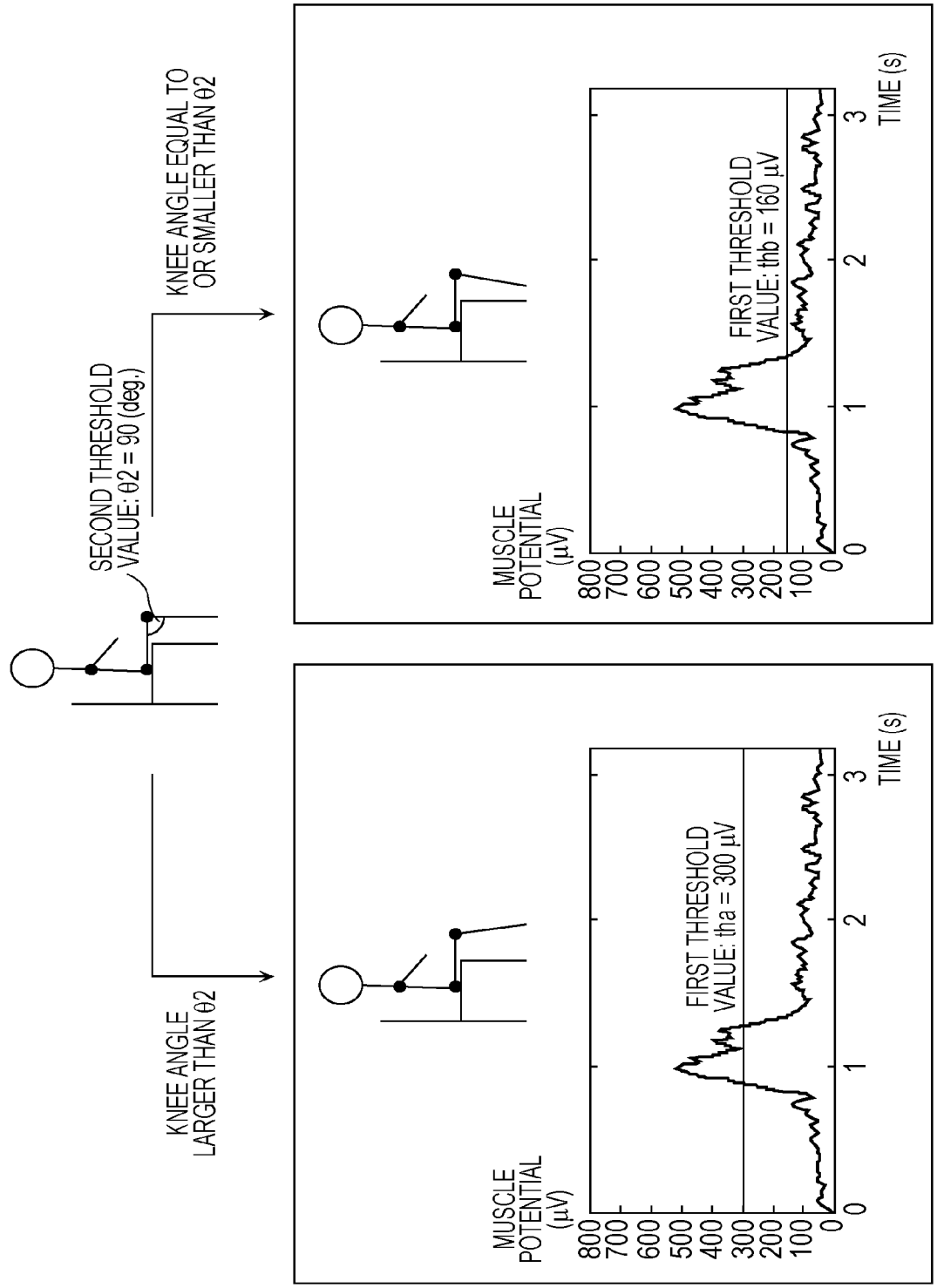
FIG. 19 illustrates an example of a first threshold value modified by a determiner of the first modification of the second embodiment.

FIG. 19 illustrates examples of the first threshold value that is modified by the determiner 105.

If the measured knee angle is larger than the second threshold value θ2 (90°, for example), the first threshold value is set to be tha=300 µV. If the measured knee angle is equal to or smaller than the second threshold value θ2, the first threshold value is set to be thb=160 µV. The first threshold value is switched between tha and thb, depending on the knee angle. The determiner 105 may pre-store the second threshold value θ2 or may read the second threshold value θ2 from an external recording medium.

Process of Standing-Up Assistance Apparatus 100A

Figure 20:
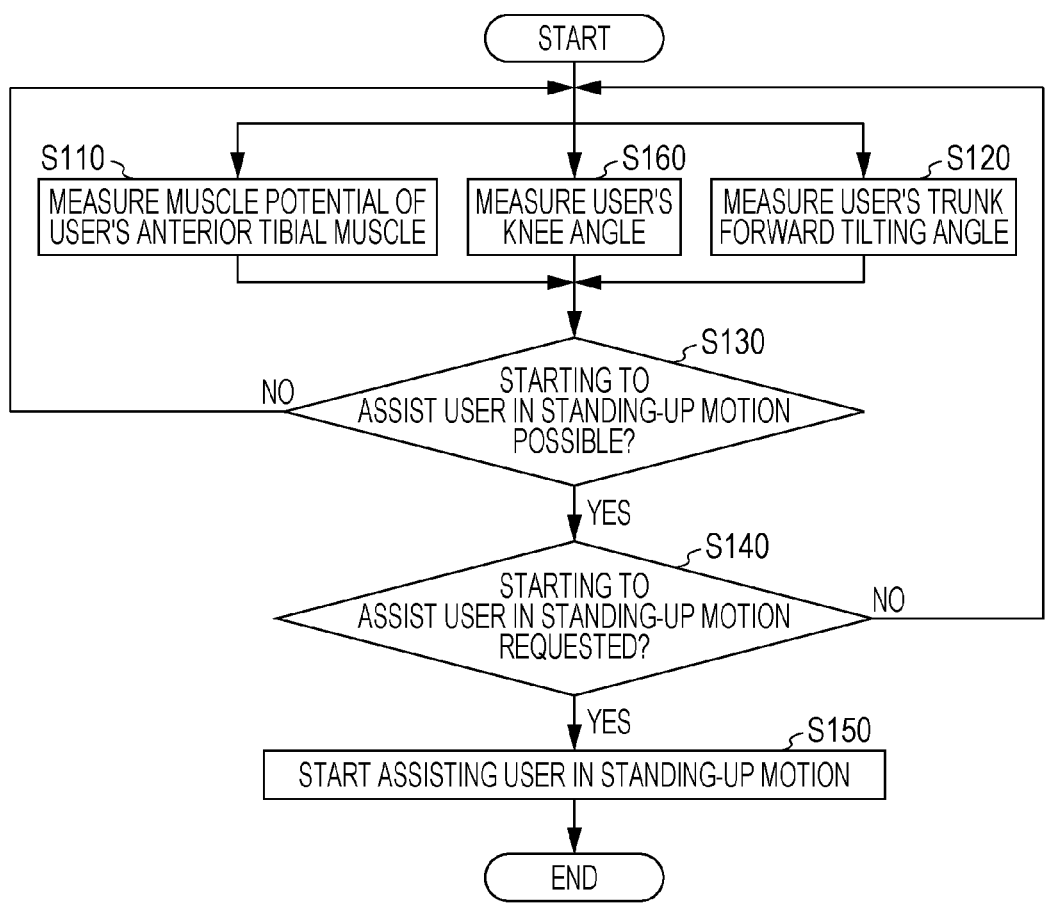
FIG. 20 is a flowchart illustrating a process of the standing-up assistance apparatus of the first modification of the second embodiment.

FIG. 20 is a flowchart illustrating a process of the standing-up assistance apparatus 100A.

The process of the standing-up assistance apparatus 100A is identical to the process of the standing-up assistance apparatus 100 of FIG. 11A including steps S110 through S150, and further includes an operation in step S160.

Step S160

The knee angle measurer 108 measures the user's knee angle. The knee angle measured herein is a value from the knee angles of the user's both legs (an average value, a minimum value, or a maximum value thereof) as the muscle potential value is calculated. The user's knee angle thus measured is used in the operation in step S130, more specifically in the operation in step S132 of FIG. 11B. More specifically, the process of the standing-up assistance apparatus 100A of the first modification includes the operations in steps S131 through S134 of FIG. 11B. A difference between the process of the standing-up assistance apparatus 100A of the first modification and the process of the first embodiment lies in the specific operation (step S132) of the determiner 105 that determines whether the anterior tibial muscle is active.

Figure 21:
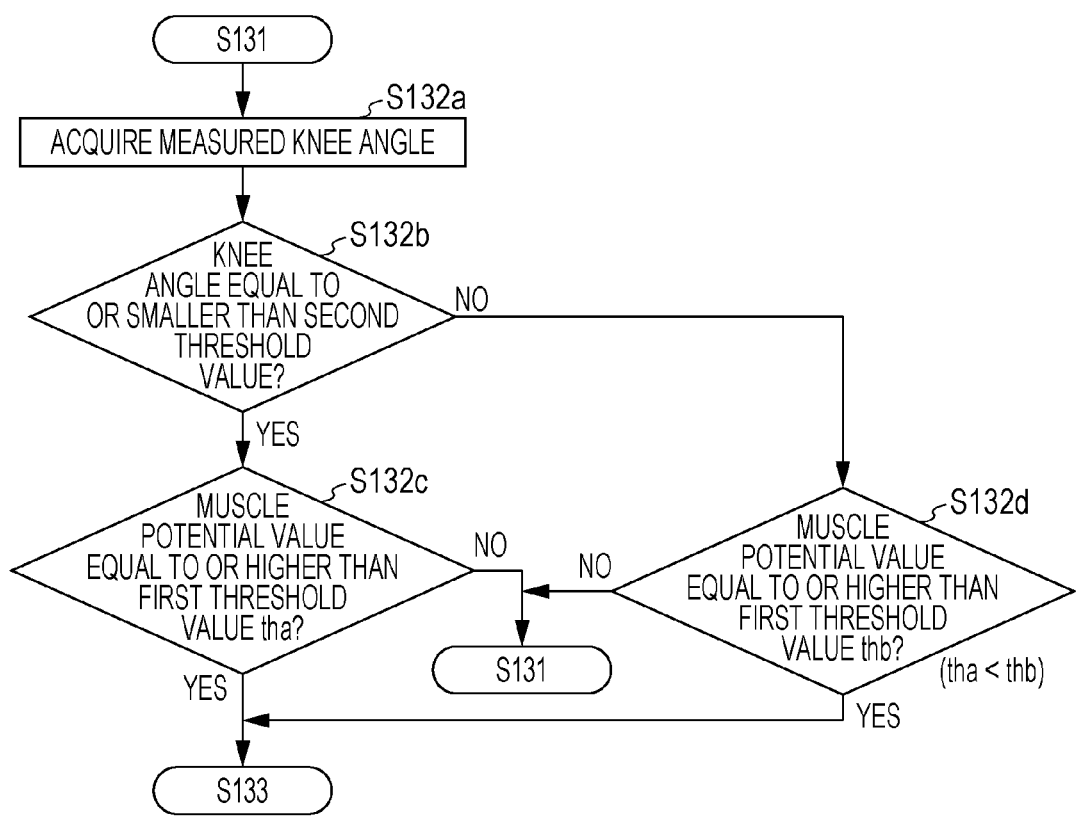
FIG. 21 is a flowchart illustrating an example of a detailed process of step S132 in accordance with the first modification of the second embodiment.

FIG. 21 is a flowchart illustrating an example of a detailed process of step S132 in accordance with the first modification.

Step S132a

The determiner 105 acquires the knee angle measured by the knee angle measurer 108.

Step S132b

The determiner 105 determines whether the knee angle acquired in step S132a is equal to or smaller than the second threshold value θ2. If the determiner 105 determines that the knee angle acquired in step S132a is equal to or smaller than the second threshold value θ2, the determiner 105 proceeds to step S132c. If the knee angle acquired in step S132a is larger than the second threshold value θ2, the determiner 105 proceeds to step S132d.

Step S132c

The determiner 105 determines whether the muscle potential value of the anterior tibial muscle acquired in step S131 is equal to or higher than the threshold value tha that is set to be the first threshold value. If the muscle potential value is determined to be equal to or higher than the threshold value tha, the determiner 105 determines that the anterior tibial muscle is active, and then performs operations in step S133 and subsequent steps of FIG. 11B. If the muscle potential value is determined to be lower than the threshold value tha, the determiner 105 determines that the anterior tibial muscle is not active, and then performs operations in step S131 and subsequent steps of FIG. 11B.

Step S132d

The determiner 105 determines whether the muscle potential value of the anterior tibial muscle acquired in step S131 is equal to or higher than the threshold value thb that is set to be the first threshold value (tha<thb). If the muscle potential value is determined to be equal to or higher than the threshold value thb, the determiner 105 determines that the anterior tibial muscle is active, and performs operations in step S133 and subsequent steps of FIG. 11B. On the other hand, if the muscle potential value is determined to be lower than the threshold value thb, the determiner 105 determines that the anterior tibial muscle is not active, and performs operations in step S131 and subsequent steps of FIG. 11B.

The operation in step S132d may be omitted from the process of FIG. 21.

Figure 22:
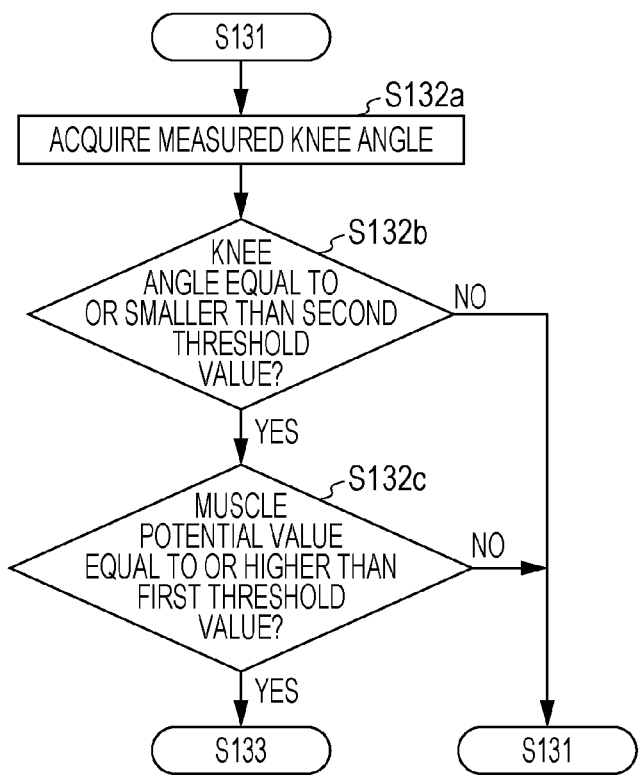
FIG. 22 is a flowchart illustrating another example of the detailed process of step S132 in accordance with the first modification of the second embodiment.

FIG. 22 is a flowchart illustrating another example of the detailed process of step S132 in accordance with the first modification.

Step S132a

The determiner 105 acquires the knee angle measured by the knee angle measurer 108.

Step S132b

The determiner 105 determines whether the knee angle acquired in step S132a is equal to or smaller than the second threshold value θ2. If the determiner 105 determines that the knee angle acquired in step S132a is equal to or smaller than the second threshold value θ2, the determiner 105 proceeds to an operation in step S132c. If the determiner 105 determines that the knee angle acquired in step S132a is larger than the second threshold value θ2, the determiner 105 determines that the anterior tibial muscle is not active, and performs operations in step S131 and subsequent steps of FIG. 11B Step S132c The determiner 105 determines whether the muscle potential value of the anterior tibial muscle acquired in step S131 is equal to or higher than the first threshold value. If the determiner 105 determines that the muscle potential value of the anterior tibial muscle acquired in step S131 is equal to or higher than the first threshold value, the determiner 105 determines that the anterior tibial muscle is active, and performs operations in step S133 and subsequent steps of FIG. 11B. On the other hand, if the determiner 105 determines that the muscle potential value of the anterior tibial muscle acquired in step S131 is lower than the first threshold value, the determiner 105 determines that the anterior tibial muscle is not active, and performs operations in step S131 and subsequent steps of FIG. 11B.

In this way, if the determiner 105 determines in step S132b that the knee angle is larger than the second threshold value θ2, the determiner 105 proceeds to the operation in step S131 regardless of the muscle potential value. More specifically, the determiner 105 of the first modification determines that starting to assist the user in the standing-up motion is possible if the first condition that the measured muscle potential value is equal to higher than the first threshold value, the second condition that the measured knee angle is equal to or smaller than the second threshold value, and the third condition that measured trunk forward tilting angle is equal to or larger than the third threshold value are concurrently satisfied.

The determiner 105 may set the first threshold value to be continuously increased as the knee angle increases. For example, the determiner 105 may set the first threshold value th1 to be th1=α×θ. Here, α is a positive numerical constant, and θ is the knee angle. If the initial value of the first threshold value is 200 µV, and the second threshold value θ2 is 90°, the value α is determined to be 200/90=2.22.

When the user tries to start up, the muscle potential value of the lower leg and the trunk forward tilting angle vary. When the process of the flowchart of FIG. 21 is performed, the user has difficulty in standing up if the first threshold value is larger, in other words, if the user's knee angle is larger. In such a case, the user may repeatedly try to stand up. As a result, the muscle potential value of the lower leg and the trunk forward tilting angle vary periodically.

When the measured muscle potential value and trunk forward tilting angle vary periodically in step S130 of FIG. 20, a notification signal to prompt the user to bend the knees is output.

Figure 23:
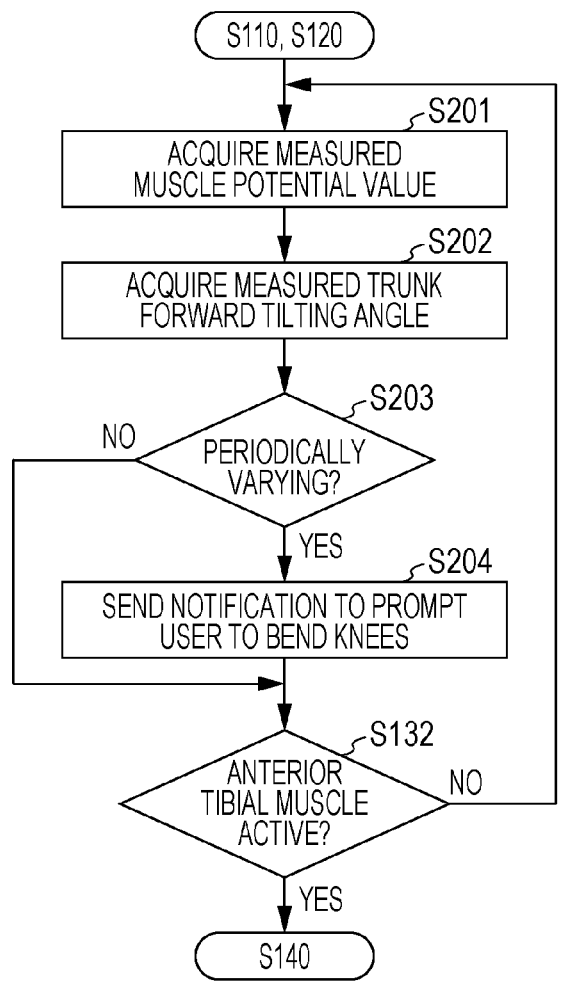
FIG. 23 is a flowchart illustrating a detailed process of step S130 of FIG. 20.

FIG. 23 is a flowchart illustrating a detailed process of step S130 of FIG. 20.

Step S201

The determiner 105 acquires the muscle potential value of the anterior tibial muscle from the memory 104.

Step S202

The determiner 105 acquires the trunk forward tilting angle from the memory 104.

Step S203

The determiner 105 determines whether the muscle potential value and the trunk forward tilting angle respectively acquired in steps S201 and S202 vary periodically.

Step S204

If the determiner 105 determines that the muscle potential value and the trunk forward tilting angle vary periodically (yes branch from step S203), the determiner 105 outputs the notification signal to prompt the user to bend the knees. For example, in response to the received notification signal, a speaker outputs a voice message prompting the user to bend the knees. Alternatively, in response to the received notification signal, a display displays a message prompting the user to bend the knees. As a result, the user bends the knees. In other words, the user's knee angle becomes smaller.

Step S132

In accordance with the flowchart of FIG. 21, the determiner 105 determines whether the anterior tibial muscle is active. If the notification is made in step S204, the knee angle becomes smaller, and is likely to be equal to or smaller than the second threshold value. In step S132c, the determiner 105 determines whether the muscle potential value is the first threshold value tha or higher (tha<thb). More specifically, the determiner 105 compares the muscle potential value with the first threshold value tha that is the lower threshold value. If the knee angle is larger than the second threshold value, the determiner 105 determines in step S132d whether the muscle potential value is equal to higher than the first threshold value thb. In other words, the determiner 105 compares the muscle potential value with the first threshold value thb that is the higher threshold value. If the determiner 105 determines in steps S132c and S132d that the muscle potential value is equal to or higher than the first threshold value (namely, yes branch from step S132), the determiner 105 performs the operation in step S140 of FIG. 20. In other words, the standing-up motion assistance starts. If the determiner 105 determines in steps S132c and S132d that the muscle potential value is lower than the first threshold value (namely, no branch from step S132), the determiner 105 repeats the operation in step S201 of FIG. 23.

If the muscle potential value of the lower leg and the trunk forward tilting angle vary periodically, the user may attempt to stand up but may be unable to stand up because of a larger knee angle. The user may thus repeat an attempt to stand up. In such a case, the notification signal prompting the user to bend the knees is output. In response to the notification signal, a voice message or a text message prompting the user to bend the knees is presented to the user. In response to the presentation, the user will bend the knees. With the knees bent, the first threshold value becomes lower, and the first condition is easy to satisfy. The determiner 105 thus determines that starting to assist in the standing-up motion is possible. The user is thus assisted in the standing-up motion by the assistance mechanism 107, and may easily stand up.

Effect

In accordance with the first modification, the first threshold value used to determine the activity of the anterior tibial muscle increases in the state that the assistance in the standing-up motion is difficult to be performed correctly because of a larger knee angle. The determiner 105 has difficulty in determining that the anterior tibial muscle is active. More specifically, given the same muscle potential value of the anterior tibial muscle, the determiner 105 is less likely to determine that starting to assist in the standing-up motion is possible when the knees are extended than when the knees are bent. As a result, the fall of the user and a failure to stand up as illustrated in FIG. 15A and FIG. 15B are controlled.

In accordance with the first modification, the first threshold value is set to be lower as the measured knee angle is smaller. Using the first threshold value that is set in response to the knee angle, the determiner 105 determines whether starting to assist the user in the standing-up motion is possible. In this way, if the knee angle is larger, assisting the user in the standing-up motion is not started without the user causing a strong tension in the lower leg. If the knee angle is smaller, assisting the user in the standing-up motion is started even with the user causing a weak tension in the lower leg. This arrangement reduces the risk illustrated in the example of FIG. 15A. More specifically, the user may extend the knees with a larger knee angle, and the assistance in the standing-up motion may start even if the tension in the user's lower leg is not strong enough. In such a case, the user could break the balance of the body and fall. Such a fall is thus controlled. The failure to stand up as illustrated in FIG. 15B is also controlled. If the user extends the knees with a larger knee angle, and the assistance in the standing-up motion starts even if the tension in the user's lower leg is not strong enough, the user could simply extend the knees in a seated state without being able to stand up. The occurrence of such an event is thus controlled.

In accordance with the first modification, the determiner 105 determines that starting to assist the user in the standing-up motion is possible if the first condition, the second condition that the measured knee angle is equal to smaller than the second threshold value, and the third condition are concurrently satisfied. In this way, if the knee angle is larger, assisting the user in the standing-up motion is not started, and if the knee angle is smaller, assisting in the standing-up motion is started. This arrangement controls the risk illustrated in FIG. 15A, and the failure to stand up as illustrated in FIG. 15B.

Second Modification

A second modification is different from the first embodiment and the first modification. In accordance with the second modification, the first threshold value th1 of the muscle potential value that is used to determine whether the anterior tibial muscle is active is modified, based on a trunk to thigh angle and knee angle during the assistance in the standing-up motion. The trunk to thigh angle is an angle made between the trunk and the thigh.

Configuration of Apparatus

Figure 24:
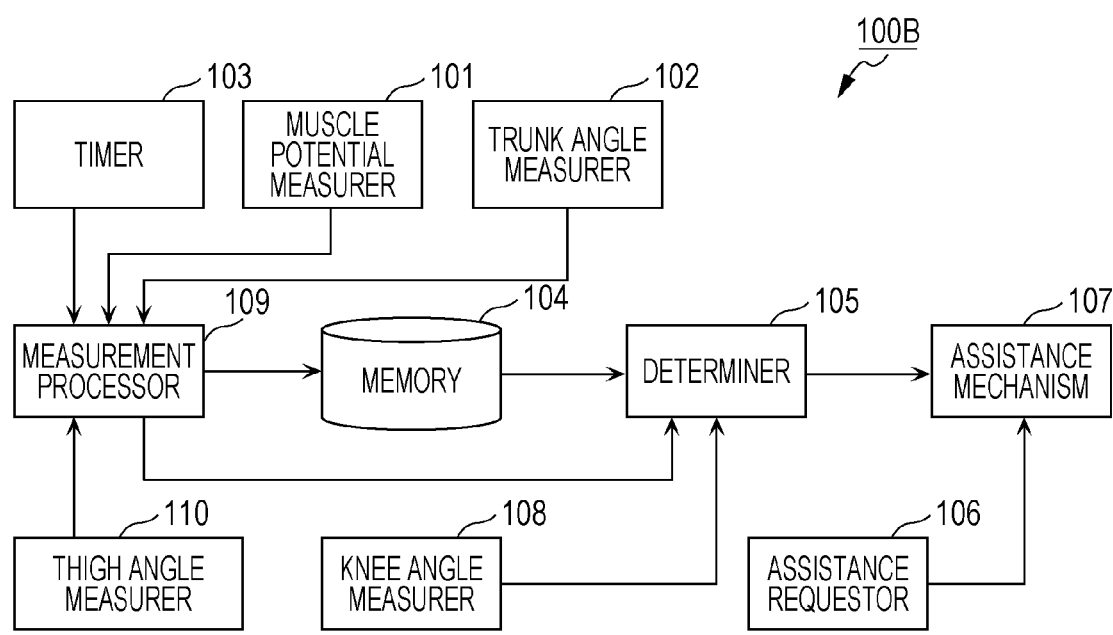
FIG. 24 is a functional block diagram of a standing-up assistance apparatus of a second modification of the second embodiment.

FIG. 24 is a functional block diagram of a standing-up assistance apparatus 100B of the second modification. The standing-up assistance apparatus 100B of the second modification includes the elements of the standing-up assistance apparatus 100A of FIG. 13 and further includes a thigh angle measurer 110 that measures the trunk to thigh angle.

Thigh Angle Measurer 110

As the trunk angle measurer 102, the thigh angle measurer 110 includes a nine-axis sensor, and measures the user's trunk to thigh angle. The thigh angle measurer 110 includes two nine-axis sensors, for example. One nine-axis sensor is secured to the user's right thigh, and the other nine-axis sensor is secured to the user's left thigh. The thigh angle measurer 110 calculates as the user's thigh angle an average value, a minimum value, or a maximum value of angles of rotation about the y axis obtained by these nine-axis sensors. The thigh angle is an angle made between a vertical direction and the user's thigh, and is about 180° when the user stands up, and about 90° when the user is seated.

The thigh angle measured by the thigh angle measurer 110 may be an angle that is calculated from a value directly obtained from the nine-axis sensor, or may be an angle that is calculated from a value corresponding to the measured value. The value corresponding to the measured value may be a value that is obtained by amplifying, rectifying, or performing a filtering operation on the directly measured value.

Measurement Processor 109

The measurement processor 109 of the second modification performs the process identical to the process of the first embodiment while calculating a trunk to thigh angle that is an angle between the user's trunk and thigh. More specifically, the measurement processor 109 calculates the trunk to thigh angle by subtracting the user's trunk forward tilting angle measured by the trunk angle measurer 102 from the user's thigh angle measured the thigh angle measurer 110. The trunk to thigh angle is thus measured. The measurement processor 109 notifies the determiner 105 of the measured trunk to thigh angle.

The standing-up assistance apparatus 100B of the second modification includes a fourth sensor that measures the trunk to thigh angle that is an angle between the user's trunk and thigh. The fourth sensor includes the trunk angle measurer 102, the thigh angle measurer 110, and part of the function of the measurement processor 109.

Determiner 105

The determiner 105 of the second modification performs the process identical to the process of the first embodiment and modifies the first threshold value th1, based on a change in each of the knee angle and the trunk to thigh angle measured during the standing-up motion. More specifically, the determiner 105 increases the first threshold value th1 to a higher value if a rate of change in the trunk to thigh angle measured during the standing-up motion is higher than a rate of change in the knee angle measured during the standing-up motion.

When the assistance mechanism 107 assists in the standing-up motion, the determiner 105 calculates a rate of change in the user's knee angle measured by the knee angle measurer 108 while also calculating a rate of change in the trunk to thigh angle notified by the measurement processor 109. The determiner 105 compares a maximum rate of change in the trunk to thigh angle with a maximum rate of change in the knee angle when the user is in the standing-up motion. If the maximum rate of change in the trunk to thigh angle is higher than the maximum rate of change in the knee angle, the determiner 105 increases the first threshold value th1 to be a higher value. The modified first threshold value th1 is used to determine the assistance start of the user's next standing-up motion.

Figure 25:
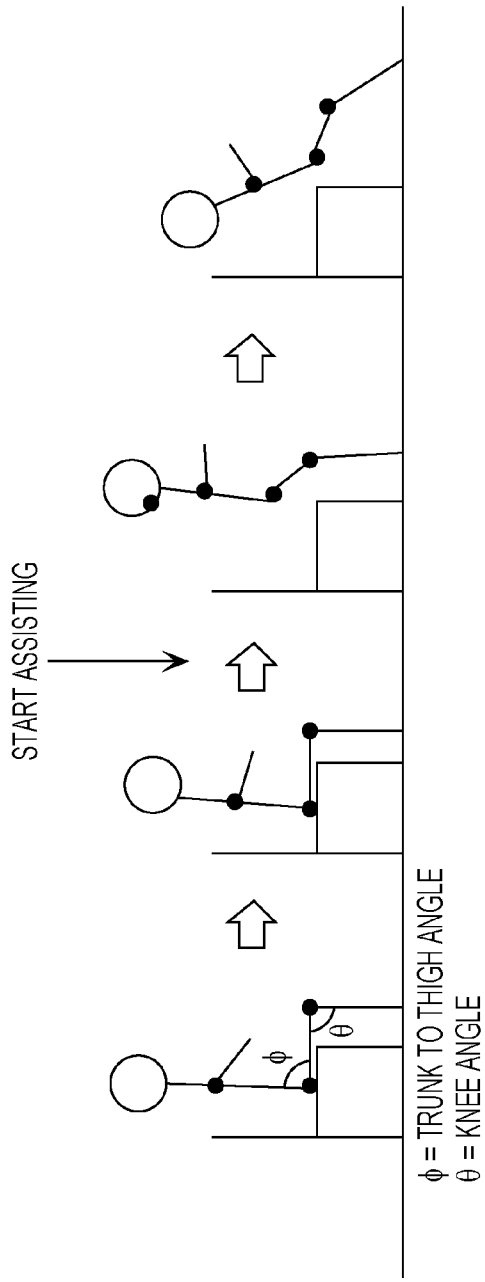
FIG. 25 illustrates an operation example in which the user breaks the balance of the body when the user is assisted in the standing-up motion.

FIG. 25 illustrates an operation example in which the user breaks the balance of the body when the user is assisted in the standing-up motion.

If the timing to start the assistance in the standing-up motion is too early, the user has not a strong tension in the lower leg at that timing, and may break the balance immediately after the assistance start. In such a case, the trunk to thigh angle φ tends to change more greatly than the knee angle θ.

Figure 26:
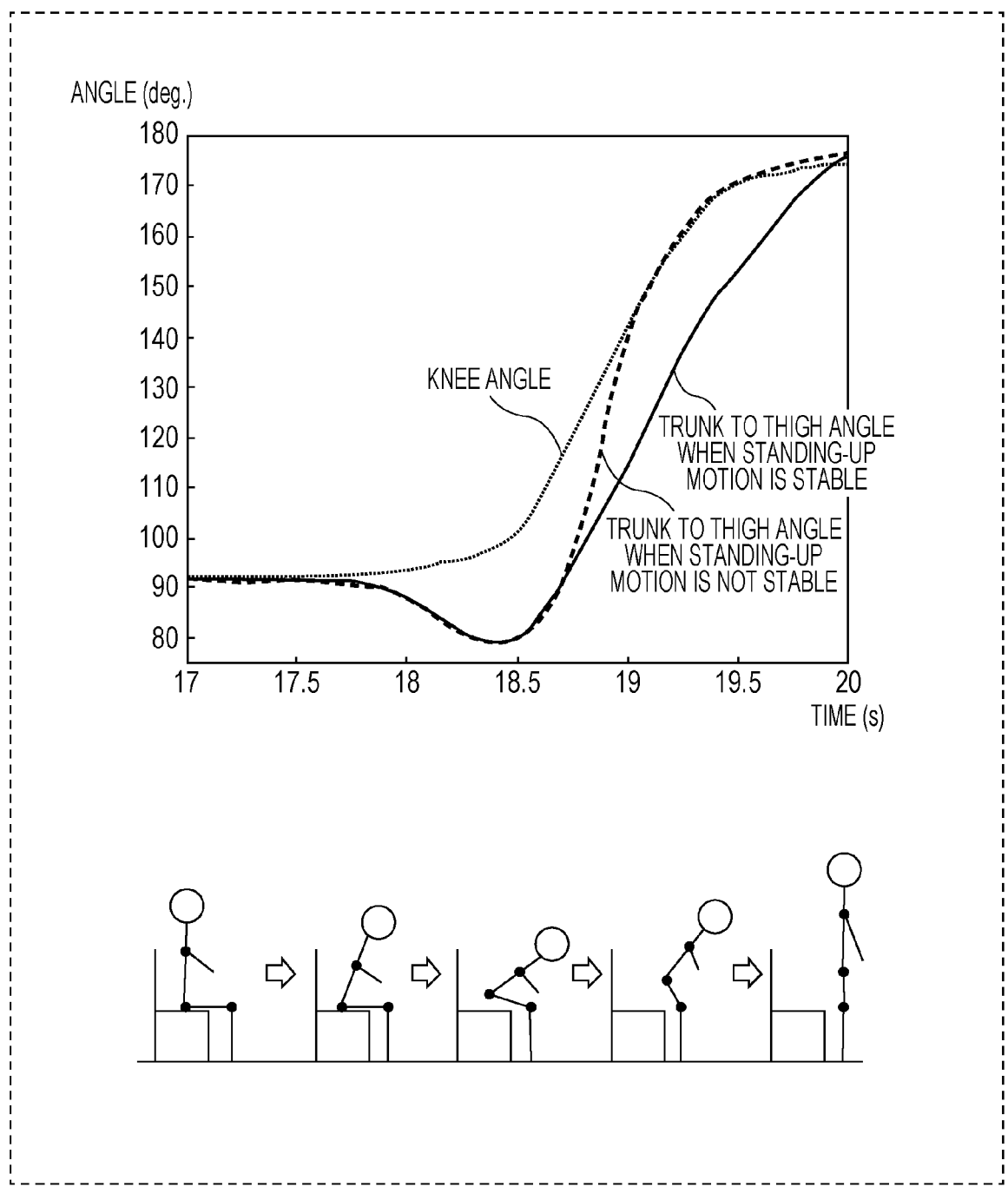
FIG. 26 illustrates an example of changes in the knee angle and a trunk to thigh angle when the user is assisted in the standing-up motion.

FIG. 26 illustrates an example of changes in the knee angle θ and the trunk to thigh angle φ when the user is assisted in the standing-up motion.

As illustrated in FIG. 26, the user may perform the standing-up motion in a stable way if the timing to start the assistance in the standing-up motion is appropriate. In such a case, both the knee angle θ and the trunk to thigh angle φ gradually increase. If the timing to start the assistance in the standing-up motion is too early, the user may perform the standing-up motion in an unstable way, leading to breaking the balance. In such a case, the trunk to thigh angle φ changes greatly in comparison with a stable standard standing-up motion. More specifically, the trunk to thigh angle φ increases more sharply than the knee angle θ.

In the standing-up assistance apparatus 100B of the second modification, the first threshold value th1 is increased to a higher value if the rate of change in the trunk to thigh angle φ is higher than the rate of change in the knee angle θ. When the assistance in the standing-up motion is started next time, the timing to start the assistance is delayed, and the assistance in the standing-up motion is thus started at an appropriate timing.

Process of Standing-Up Assistance Apparatus 100B

Figure 27:
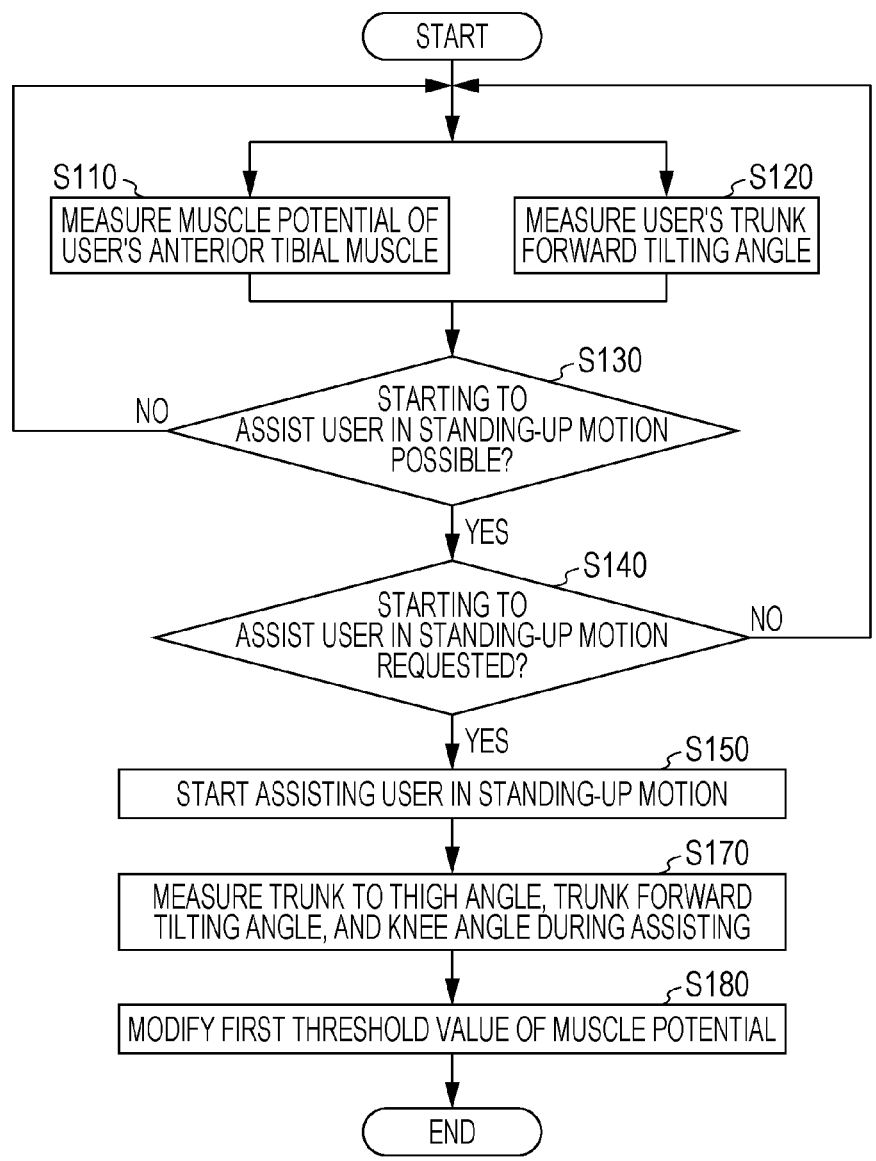
FIG. 27 is a flowchart illustrating of a process of a standing-up assistance apparatus of the second modification of the second embodiment.

FIG. 27 is a flowchart illustrating of a process of the standing-up assistance apparatus 100B of the second modification.

The process of the standing-up assistance apparatus 100B includes the operations in steps S110 through S150 of the process of the standing-up assistance apparatus 100 of FIG. 11A, and further includes operations in steps S170 and S180.

Step S170

The thigh angle measurer 110, the trunk angle measurer 102, and the knee angle measurer 108 in the standing-up assistance apparatus 100B measure the thigh angle, the trunk forward tilting angle, and the knee angle when the assistance in the standing-up motion is performed. These angles may be measured each time the second time interval has elapsed. The measurement processor 109 then calculates the trunk to thigh angle for each combination of the knee angle and trunk forward tilting angle measured at the same timing. In this way, the trunk to thigh angle and the knee angle are measured each time the second time interval has elapsed.

Step S180

The determiner 105 modifies the first threshold value th1 for use in determining whether the anterior tibial muscle is active, based on the rate of change in each of the trunk to thigh angle and knee angle measured in step S170 during the standing-up motion.

Detailed Process of Determiner 105

Figure 28:
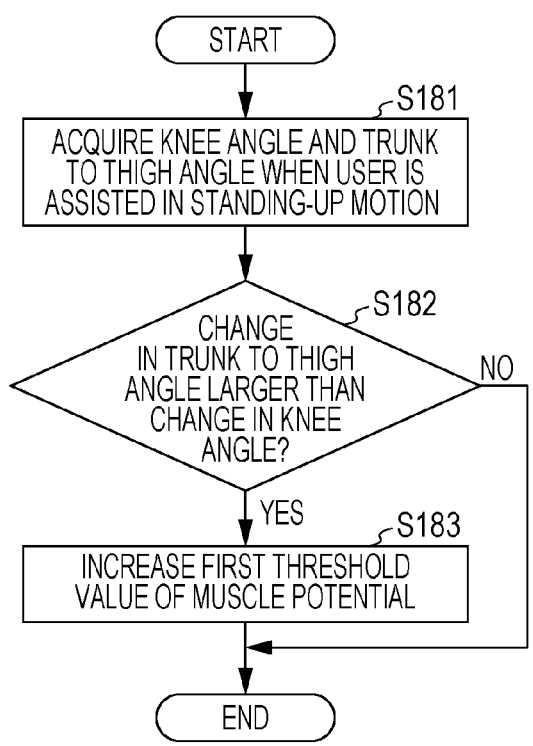
FIG. 28 is a flowchart illustrating a detailed process of step S180 of FIG. 27.

FIG. 28 is a flowchart illustrating a detailed process of step S180 of FIG. 27.

Step S181

During a time period throughout which the assistance in the standing-up motion is performed, the determiner 105 acquires the trunk to thigh angle from the measurement processor 109 and the knee angle from the knee angle measurer 108. The time period throughout which the assistance in the standing-up motion is performed may be a time period from the start of the assistance in the standing-up motion until when a predetermined time has elapsed. More specifically, during the time period, the determiner 105 acquires the trunk to thigh angle and the knee angle each time the second time interval has elapsed.

Step S182

The determiner 105 determines whether a change in the trunk to thigh angle is larger than a change in the knee angle when the assistance in the standing-up motion is performed. If the determiner 105 determines that the change in the trunk to thigh angle is higher, the determiner 105 proceeds to step S183. If the determiner 105 determines that the change in the trunk to thigh angle is not higher, the determiner 105 ends the modification operation of the first threshold value.

More specifically, the determiner 105 determines whether a maximum rate of change in the trunk to thigh angle is higher than a maximum rate of change in the knee angle when the assistance in the standing-up motion is performed. Alternatively, if a change in the trunk to thigh angle is larger by a specific value than a change in the knee angle for a specific time width, the determiner 105 may determine that the change in the trunk to thigh angle is larger.

The determiner 105 may perform the determination operation in step S182, based on the user's the trunk to thigh angle only. More specifically, if a change in the trunk to thigh angle for a specific time width is larger than a predetermined threshold value, the determiner 105 may determine that the change in the trunk to thigh angle is larger. If the user breaks the balance during the standing-up motion, the user's body may be rocking backwards and forwards. If a change in the trunk forward tilting angle is not a monotonous increase but has a peak value, the determiner 105 may determine that the change in the trunk to thigh angle is larger.

The determiner 105 thus correctly determines whether the user has been correctly assisted in the standing-up motion, by observing the change in each of the user's trunk to thigh angle and knee angle when the assistance in the standing-up motion is performed.

Step S183

When the determiner 105 determines that the change in the trunk to thigh angle is larger, in other words, the determiner 105 determines that the user is not correctly assisted in the standing-up motion, the determiner 105 increases the first threshold value th1 of the muscle potential by a specific value.

Effect

In accordance with the second modification, the first threshold value th1 used to determine whether the assistance in the next standing-up motion is to be started is increased to a larger value if a change in the trunk to thigh angle is larger during the assistance in the standing-up motion. If a higher tension is not caused in the lower leg during the next standing-up motion, the assistance in the standing-up motion is not started. The assistance in the standing-up motion is thus started at an appropriate timing, thereby reducing the risk that the user breaks the balance during the assistance in the standing-up motion.

The user is considered to be in an unstable state in the standing-up motion if the rate of change in the trunk to thigh angle measured during the standing-up motion is higher than the rate of change in the knee angle measured during the standing-up motion. In accordance with the second modification, the first threshold value is increased to a higher value if the rate of change in the trunk to thigh angle measured during the standing-up motion is higher than the rate of change in the knee angle measured during the standing-up motion. When the user stands up next time, the assistance in the standing-up motion is started at the timing that is determined using the modified first threshold value. This arrangement delays the timing of starting the assistance in the standing-up motion, and as a result, the user is able to stand up in a stable way.

OTHER EMBODIMENTS

The standing-up assistance apparatuses of one or more embodiments and the modifications thereof have been described. The present disclosure is not limited to the embodiments and the modifications thereof. A modification obvious to those skilled in the art may be applied to the embodiments and the modifications thereof, and some elements of the embodiments and the modifications thereof may be combined to form a new embodiment. As long as those modifications do not depart from the spirit of the present disclosure, the modifications fall within the scope of the present disclosure.

In accordance with the embodiments and the modifications thereof, a determination is made as to whether a request to start the assistance in the standing-up motion has been made after determining that starting to assist in the standing-up motion is possible as illustrated in FIG. 11A, FIG. 20, and FIG. 27. The order of determination operations may be reversed.

In accordance with the embodiments and the modifications thereof, the specific values of the first threshold value, the second threshold value, and the third threshold value are specifically described. Those values are described for exemplary purposes only, and the present disclosure is not limited to those values. Each of the first threshold value, the second threshold value, and the third threshold value may take any value.

In accordance with the embodiments and the modifications thereof, the muscle potential of the anterior tibial muscle is measured. Alternatively, the muscle potential of another muscle, such as of the medial great muscle, may be measured instead of the anterior tibial muscle. The muscle potential of the left leg or the right leg only may be measured instead of measuring the muscle potentials of both legs. Similarly, the thigh angle of the left leg or the right leg only may be measured instead of measuring the thigh angles of both legs. Alternatively, the muscle potential and the thigh angle of the user's dominant leg may be measured.

In accordance with the second modification, in order to determine whether a change in the trunk to thigh angle is larger or not, a determination is made as to whether the maximum rate of change in the trunk to thigh angle during the standing-up motion is higher than the maximum rate of change in the knee angle during the standing-up motion. The present disclosure is not limited to this method. Another method may be used to determine whether the change in the trunk to thigh angle is larger or not. For example, a determination may be made as to whether the average of rates of change in the trunk to thigh angle within a time segment of the period of the standing-up motion is higher than the average of rates of change in the knee angle within that time segment of the period of the standing-up motion. The time segment of the period may be a duration of time within the period of the standing-up motion excluding the beginning portion and ending portion of the period.

In accordance with the embodiments and the modifications thereof, the elements may be implemented by using dedicated hardware or by executing a software program appropriate for each element. Each element may be implemented by a program executing unit, such as a central processing unit (CPU) or a processor, which reads and executes the software program stored on a recording medium, such as a hard disk or a semiconductor memory. The software program that implements the standing-up assistance apparatus of each of the embodiments and the modifications thereof is a computer program that causes a computer to execute each step included in the flowcharts of FIG. 1B, FIG. 11A, FIG. 11B, FIG. 12B, FIG. 20 through FIG. 23, FIG. 27 and FIG. 28.

In accordance with the present disclosure, some or all of the units, apparatuses, members, or units, or some or all of the functional blocks of the block diagrams of FIG. 1A, FIG. 2, FIG. 12A, FIG. 13, and FIG. 24 may be implemented using one or more electronic circuits including a semiconductor device, an integrated circuit (IC), or a large scale integration (LSI). The LSI or the IC may be integrated into a single chip or multiple chips. The functional blocks excluding the memories may be integrated into a single chip. The LSI and IC are quoted herein, but the LSI may be referred to as a system LSI, a very large scale integration (VLSI), or an ultra large scale integration (ULSI), depending on a difference in the degree of integration. A field programmable gate array (FPGA) or a reconfigurable logic device may be used for the same purposes. The FPGA is programmable after the manufacture of the LSI. The reconfigurable logic device is reconfigurable in terms of the connection and configuration inside the LSI.

The functions or operations of some or all of the units, apparatuses, members, and units may be implemented using software. In this case, the software may be recorded on non-transitory recording media including one or more of read-only memories (ROMs), optical disks, and hard disk drives. When a processor executes the software, a function identified by the software is performed by the processor or a peripheral device. A system or apparatus may include one or more non-transitory recording media having recorded the software thereon, a processor, and a hardware device in use, such as an interface.

The standing-up assistance apparatuses of the disclosure find applications in an assist suit or a robot, each assisting in a standing-up motion.

What is claimed is:

1. A standing-up assistance apparatus, comprising:
   a first sensor that measures a muscle potential of a lower leg of a user;
   a second sensor that measures a knee angle of the user;
   a processor that determines whether starting to assist the user in a standing-up motion from a seated state is seated possible based on the measured muscle potential and the measured knee angle; and
   an assistance mechanism,
   wherein the processor outputs an instruction signal if the processor determines that starting to assist the user in the standing-up motion is possible, wherein the first sensor continues to measure the muscle potential of the lower leg of the user and the second sensor continues to measure the knee angle of the user if the processor determines that starting to assist the user in the standing-up motion is not possible, and
   wherein the assistance mechanism starts to assist the user in the standing-up motion when the assistance mechanism receives the instruction signal from the processor.

2. The standing-up assistance apparatus according to claim 1, wherein the first sensor measures a muscle potential of an anterior tibial muscle of the user as the muscle potential of the lower leg of the user.

3. The standing-up assistance apparatus according to claim 1, wherein the assistance mechanism assists the user in the standing-up motion by assisting the user to extend the user's knees.

4. The standing-up assistance apparatus according to claim 1, wherein the processor determines that starting to assist the user in the standing-up motion is possible if a first condition that the measured muscle potential is equal to or higher than a first threshold value and a second condition that the measured knee angle is equal to or smaller than a second threshold value are concurrently satisfied.

5. The standing-up assistance apparatus according to claim 4, wherein the second threshold value is 60° or higher and 100° or lower.

6. The standing-up assistance apparatus according to claim 1, wherein the knee angle of the user measured by the second sensor is the knee angle of the user's left knee or the knee angle of the user's right knee, whichever is smaller.

7. The standing-up assistance apparatus according to claim 1, wherein the processor determines whether starting to assist the user in the standing-up motion from the seated state is possible, without using output data of a sensor disposed at a hip part of the user.

8. A standing-up assistance apparatus, comprising:
   a first sensor that measures a muscle potential of a lower leg of a user;
   a second sensor that measures a knee angle of the user;
   a third sensor that measures a trunk forward tilting angle of the user;
   a processor that determines whether starting to assist the user in a standing-up motion from a seated state is seated possible based on the measured muscle potential, the measured knee angle, and the measured trunk forward tilting angle; and
   an assistance mechanism;
   wherein the processor outputs an instruction signal if the processor determines that starting to assist the user in the standing-up motion is possible, wherein the first sensor continues to measure the muscle potential of the lower leg of the user and the second sensor continues to measure the knee angle of the user if the processor determines that starting to assist the user in the standing-up motion is not possible, and wherein the assistance mechanism starts assisting the user in the standing-up motion when the instruction signal is output from the processor.

9. The standing-up assistance apparatus according to claim 8, wherein the trunk forward tilting angle is an angle made between a vertical direction and the trunk of the user, and increases as the user's trunk tilts more forward.

10. The standing-up assistance apparatus according to claim 9, wherein the processor determines that starting to assist the user in the standing-up motion is possible if a first condition that the measured muscle potential is equal to or higher than a first threshold value, a second condition that the measured knee angle is equal to or smaller than a second threshold value, and a third condition that the measured trunk forward tilting angle is equal to or larger than a third threshold value are concurrently satisfied.

11. The standing-up assistance apparatus according to claim 10, wherein the assistance mechanism comprises a fourth sensor that measures a trunk to thigh angle that is made between the user's trunk and thigh, and wherein the processor modifies the first threshold value in response to a change in each of the knee angle and the trunk to thigh angle measured during the standing-up motion.

12. The standing-up assistance apparatus according to claim 11, wherein the processor increases the first threshold value to a larger value if a rate of change in the trunk to thigh angle measured during the standing-up motion is higher than a rate of change in the knee angle measured during the standing-up motion.

13. The standing-up assistance apparatus according to claim 9, wherein the processor sets the first threshold value to be lower as the measured knee angle becomes smaller, and determines that starting to assist the user in the standing-up motion is possible if a first condition that the measured muscle potential is equal to or higher than a first threshold value, and a third condition that the measured trunk forward tilting angle is equal to or larger than a third threshold value are concurrently satisfied.

14. The standing-up assistance apparatus according to claim 13, wherein the processor outputs a notification signal to prompt the user to bend the user's knees if each of the measured muscle potential and the measured trunk forward tilting angle changes periodically.

15. The standing-up assistance apparatus according to claim 8, wherein the processor determines whether starting to assist the user in the standing-up motion from the seated state is possible, without using output data of a sensor disposed at a hip part of the user.

16. A standing-up assistance apparatus, comprising:
a first sensor that measures a muscle potential of a lower leg of a user;
a second sensor that measures a knee angle of the user; and
a processor that determines whether starting to assist the user in a standing-up motion from a seated state is seated possible based on the measured muscle potential and the measured knee angle,
wherein the processor outputs an instruction signal if the processor determines that starting to assist the user in the standing-up motion is possible, and wherein the first sensor continues to measure the muscle potential of the lower leg of the user and the second sensor continues to measure the knee angle of the user if the processor determines that starting to assist the user in the standing-up motion is not possible.

17. The standing-up assistance apparatus according to claim 16, wherein the processor determines that starting to assist the user in the standing-up motion is possible if a first condition that the measured muscle potential is equal to or higher than a first threshold value and a second condition that the measured knee angle is equal to or smaller than a second threshold value are concurrently satisfied.

18. The standing-up assistance apparatus according to claim 16, wherein the processor determines whether starting to assist the user in the standing-up motion from the seated state is possible, without using output data of a sensor disposed at a hip part of the user.

19. A standing-up assistance method, comprising:
measuring a muscle potential of a lower leg of a user;
measuring a knee angle of the user;
determining whether starting to assist the user in a standing-up motion from a seated state is seated possible based on the measured muscle potential and the measured knee angle; and
starting to assist the user in the standing-up motion if starting to assist the user in the standing-up motion is determined to be possible,
wherein the muscle potential of the lower leg of the user and the knee angle of the user continue to be measured if starting to assist the user in the standing-up motion is determined to not be possible.

20. The standing-up assistance method according to claim 19, wherein starting to assist the user in the standing-up motion is determined to be possible if a first condition that the measured muscle potential is equal to or higher than a first threshold value and a second condition that the measured knee angle is equal to or smaller than a second threshold value are concurrently satisfied.

21. The standing-up assistance method according to claim 19, wherein whether starting to assist the user in the standing-up motion from the seated state is possible is determined, without using output data of a sensor disposed at a hip part of the user.

22. A non-transitory computer-readable recording medium being a non-volatile and storing a control program causing an apparatus including a processor to perform a process, the process comprising:
measuring a muscle potential of a lower leg of a user;
measuring a knee angle of the user; and
determining whether starting to assist the user in a standing-up motion from a seated state is seated possible based on the measured muscle potential and the measured knee angle, and outputting an instruction signal to an assistance mechanism that assists the user in the standing-up motion if starting to assist the user in the standing-up motion is determined to be possible,
wherein the muscle potential of the lower leg of the user and the knee angle of the user continue to be measured if starting to assist the user in the standing-up motion is determined to not be possible.

23. The non-transitory computer-readable recording medium according to claim 22, wherein the processor determines that starting to assist the user in the standing-up motion is possible if a first condition that the measured muscle potential is equal to or higher than a first threshold value and a second condition that the measured knee angle is equal to or smaller than a second threshold value are concurrently satisfied.

24. The non-transitory computer-readable recording medium according to claim 22, wherein the processor determines whether starting to assist the user in the standing-up motion from the seated state is possible, without using output data of a sensor disposed at a hip part of the user.

* * * * *